(12) United States Patent
Gotoh

(10) Patent No.: US 10,835,198 B2
(45) Date of Patent: Nov. 17, 2020

(54) X-RAY DEVICE, CONTROL DEVICE AND CONTROL METHOD FOR CONTROLLING THE SAME, AND CONTROL PROGRAM

(71) Applicant: Shimadzu Corporation, Kyoto (JP)

(72) Inventor: Keita Gotoh, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 29 days.

(21) Appl. No.: 16/227,359

(22) Filed: Dec. 20, 2018

(65) Prior Publication Data

US 2020/0196976 A1 Jun. 25, 2020

(51) Int. Cl.
*A61B 6/00* (2006.01)
(52) U.S. Cl.
CPC ............ *A61B 6/548* (2013.01); *A61B 6/4266* (2013.01); *A61B 6/4494* (2013.01); *A61B 6/541* (2013.01)
(58) Field of Classification Search
CPC ..... A61B 6/548; A61B 6/4266; A61B 6/4494; A61B 6/54
See application file for complete search history.

(56) References Cited

U.S. PATENT DOCUMENTS

2007/0165783 A1\* 7/2007 Abu Tabanjeh ..... A61B 6/4233
378/116

FOREIGN PATENT DOCUMENTS

| JP | 2002-191586 A | | 7/2002 |
|---|---|---|---|
| JP | 2008-099808 A | | 5/2008 |
| JP | 2008-142111 A | | 6/2008 |
| JP | 2008142111 A | \* | 6/2008 |
| JP | 2009-045432 A | | 3/2009 |
| JP | 2012-105895 A | | 6/2012 |

OTHER PUBLICATIONS

Notification of Reasons for Refusal dated Jun. 16, 2019 for Japanese Patent application No. 2016-117949, submitted with a machine translation.

\* cited by examiner

*Primary Examiner* — Courtney D Thomas
(74) *Attorney, Agent, or Firm* — Muir Patent Law, PLLC

(57) ABSTRACT

An object of the present invention is to provide an X-ray device that can automatically choose an X-ray detector suitable for a purpose from usable X-ray detectors when there is a possibility that the usable X-ray detector is dynamically changed at timing of performing inspection, a control device and a control method for controlling the X-ray device, and a control program. For example, a flat panel X-ray detector (FPD) is chosen based on imaging order information such as a recommended detector size, and the corresponding FPD is chosen based on the usable FPD among these FPDs. Thus, in the case that there is a possibility that the usable FPD is dynamically changed at timing of imaging, the FPD suitable for the purpose of imaging order is automatically selected from the usable FPDs.

15 Claims, 7 Drawing Sheets

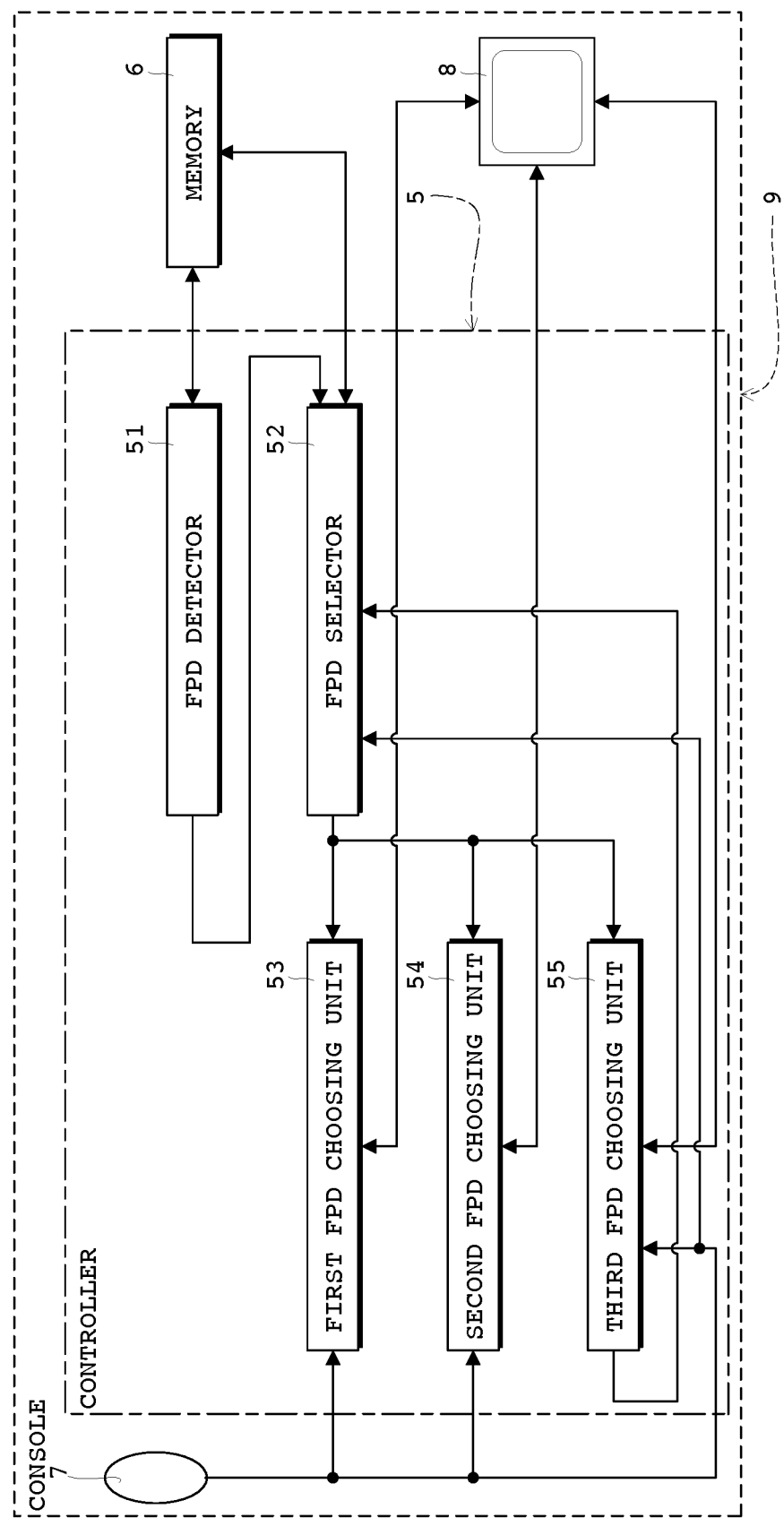

X-RAY DEVICE, CONTROL DEVICE AND CONTROL METHOD FOR CONTROLLING THE SAME, AND CONTROL PROGRAM

TECHNICAL FIELD

The present invention relates to an X-ray device including an X-ray tube that emits an X-ray and an X-ray detector that detects the emitted X-ray, a control device and a control method for controlling the same, and a control program.

BACKGROUND ART

Inspection in the X-ray device will be described by taking imaging as an example. In an X-ray imaging device including an X-ray tube, a plurality of X-ray detectors, and a console that controls the X-ray detectors, when imaging is performed based on imaging order information, it is necessary to choose and designate the X-ray detector used during the imaging from the plurality of X-ray detectors. Examples of the imaging order information include a size of a test object, a size of a region of interest that is an imaging target, a region (imaging region) of the region of interest, a technique (for example, a front of a chest and a side of a chest) of imaging the imaging region from a direction, and sensitivity of the X-ray detector.

For the designation of the X-ray detector, there are a method (the former method) in which an operator explicitly chooses the X-ray detector from the usable X-ray detectors before the imaging, and a method (the latter method) for designating the X-ray detector to be used based on the detector ID associated with the imaging order information chosen by the console during the imaging while previously associating the imaging order information with information about the X-ray detector (hereinafter, referred to as "detector ID").

In the latter method, for example, a large X-ray detector is associated with the imaging order relating to a normal imaging region such as a chest and an abdomen, and a small X-ray detector is associated with the imaging order for limbs and children, whereby the imaging can be performed using an X-ray detector having an optimum size corresponding to the imaging region without requiring an operation to manually switch the X-ray detector to be used before the imaging. In recent years, a digital X-ray detector capable of communicating with a console is used as the X-ray detector, and a flat panel X-ray detector (FPD: Flat Panel Detector) is used as the digital X-ray detector.

In addition to the former method and the latter method, in imaging using a standing position imaging stand or a recumbent position imaging table, there is also a method in which a Bucky device detects a detector ID of a flat panel X-ray detector (hereinafter referred to as "FPD") and automatically designates the FPD as the X-ray detector to be used when the FPD is accommodated in the Bucky device mounted on the standing position imaging stand or the recumbent position imaging table (for example, refer to Patent Literature 1).

In an X-ray imaging device capable of conducting wireless communication (radio communication), an X-ray detector is chosen from the plurality of X-ray detectors based on the imaging order information (such as spatial resolution and a size of a region of interest) (for example, refer to Patent Literature 2). In particular, Patent Literature 2: JP 2002-191586 A discloses in the paragraph [0016] that another low-profile X-ray detector is separately arranged for a purpose of imaging of four limbs or the like.

CITATION LIST

Patent Literature

Patent Literature 1: JP 2012-105895 A
Patent Literature 2: JP 2002-191586 A

SUMMARY OF INVENTION

Technical Problem

However, the conventional example having such configuration has the following problem.

That is, for example, when the imaging order information is previously associated with the detector ID as in Patent Literature 1: JP 2012-105895 A, the associated detector ID is associated with the X-ray detector assumed to be used on the X-ray imaging device.

Meanwhile, the X-ray detectors typified by the FPD and the like are of a portable type, the X-ray detector capable of conducting wireless communication as in Patent Literature 2: JP 2002-191586 A is becoming common, and one X-ray detector can be shared by a plurality of X-ray imaging devices. In the case of adopting the above method, one X-ray detector cannot simultaneously be used by the plurality of X-ray imaging devices, but can be used only by one X-ray imaging device. Thus, the X-ray detector cannot be used from the X-ray imaging device except for the X-ray imaging device in which the X-ray detector is currently used. For this reason, in the X-ray imaging device in which the X-ray detector is used, the usable X-ray detector may be different depending on the situation.

In the case that the X-ray detector is shared by the plurality of X-ray imaging devices, the associated X-ray detector may not be used in the associated X-ray imaging device while being used by another X-ray imaging device. As in this situation, the X-ray detector is not necessarily usable at timing of performing actual imaging.

For the imaging method in which a Bucky device (imaging by a typical imaging technique) is not used, and for imaging in the imaging device in which the Bucky device such as a device for round visit does not originally exist, the X-ray detector stored in the Bucky device cannot be automatically chosen. Additionally, when the largest-size X-ray detector is constantly and automatically chosen among the usable X-ray detectors, the range (the range of the imaging region) of the X-ray detector necessary for the imaging can be covered. However, although weight reduction of the X-ray detector progresses due to advance in technology, there are many X-ray detectors having weights of the order of several kilograms, and there are also needs to use a small X-ray detector as much as possible when a small technician or a female technician performs the imaging.

The present invention has been made in view of the above circumstances, and an object of the present invention is to provide an X-ray device that can automatically choose an X-ray detector suitable for a purpose from usable X-ray detectors when there is a possibility that the usable X-ray detector is dynamically changed at timing of performing inspection, a control device and a control method for controlling the X-ray device, and a control program.

Solution to Problem

The present invention adopts the following constitution in order to attain the object.

According to one aspect of the present invention, an X-ray device includes: an X-ray tube that emits an X-ray; an X-ray detector that detects the emitted X-ray; an X-ray detector detecting unit that detects the X-ray detector that is usable; and an X-ray detector selecting unit that selects the X-ray detector to be chosen based on inspection order information. The X-ray detector selected by the X-ray detector selecting unit is chosen among the X-ray detectors detected by the X-ray detector detecting unit.

The X-ray device of the present invention includes the X-ray detector detecting unit that detects the usable X-ray detector and the X-ray detector selecting unit that selects the X-ray detector to be chosen based on the inspection order information. The X-ray detector selecting unit chooses the X-ray detector among the X-ray detectors detected by the X-ray detector detecting unit based on the inspection order information. In this way, the corresponding X-ray detector is chosen among the usable X-ray detectors based on the inspection order information, so that the X-ray detector suitable for the purpose (of the inspection order) can automatically be chosen from the usable X-ray detectors in the case that there is a possibility that the usable X-ray detector can dynamically be changed at the timing of performing the inspection. Consequently, a burden on an operator can be reduced during an inspection operation.

In the X-ray device according to the present invention described above, an example of the inspection order information is an X-ray detector size (hereinafter, also referred to as "recommended detector size") necessary for the inspection, and the X-ray detector selecting unit selects the X-ray detector based on the X-ray detector size (recommended detector size). When the X-ray detector having the same size as the X-ray detector size (recommended detector size) is usable, the X-ray detector having the same size as the X-ray detector size can be chosen. In particular, as described later, when one X-ray detector having the same size exists among the usable X-ray detectors, the corresponding X-ray detector is chosen.

When one usable X-ray detector exists, the X-ray detector is chosen as follows. That is, the X-ray device according to the present invention described above includes a first X-ray detector choosing unit that chooses the corresponding X-ray detector when one X-ray detector having the same size that is selected by the X-ray detector selecting unit exists among the X-ray detectors detected by the X-ray detector detecting unit.

When a plurality of X-ray detectors having the same size exist, the operator may manually set the priority for using the X-ray detector, and the X-ray detectors may automatically be chosen according to the priority. That is, the X-ray device according to the present invention described above includes a priority setting unit that sets the priority for using the X-ray detector and a second X-ray detector choosing unit that chooses the X-ray detector according to the priority set by the priority setting unit. This case is useful for the case that the plurality of X-ray detectors having the same size exist among the X-ray detectors detected by the X-ray detector detecting unit, and the second X-ray detector choosing unit chooses the X-ray detector having top priority set by the priority setting unit from the plurality of corresponding X-ray detectors. For example, when the priority is set based on the sensitivity of the X-ray detector, the X-ray detector having the highest sensitivity is set to the top priority, and the X-ray detector is set to the lower priority with decreasing sensitivity. Consequently, the X-ray detector having high sensitivity can preferentially be used from the usable X-ray detectors, and the X-ray irradiation dose can be reduced with increasing sensitivity, which leads to the reduction of the radiation exposure of the test object (patient).

When the plurality of X-ray detectors having the same size exist, as described above, the X-ray detector having the top priority is chosen from the plurality of X-ray detectors having the same size. When the priority is set based on the sensitivity of the X-ray detector, the X-ray detector is chosen in the order of "usable X-ray detector"→"X-ray detector size (recommended detector size)"→"sensitivity of X-ray detector"→"priority".

The X-ray device includes a third X-ray detector choosing unit that performs the following choice when an example of the inspection order information is the X-ray detector size (recommended detector size) necessary for the inspection. That is, when the X-ray detector having the same size as the X-ray detector size (recommended detector size) is usable, the third X-ray detector choosing unit chooses the X-ray detector having the same size. On the other hand, when the X-ray detector having the same size as the X-ray detector size (recommended detector size) is unusable and the X-ray detector having the size larger than the X-ray detector size (recommended detector size) is usable, the third X-ray detector choosing unit chooses the smallest-size X-ray detector from the corresponding X-ray detectors having the larger size. When the X-ray detector having the same size as the X-ray detector size (recommended detector size) is unusable and the X-ray detector having the size larger than the X-ray detector size (recommended detector size) is usable, as described also in "Technical Problem", the range (the range of the imaging region) necessary for the inspection (including the fluoroscopy and the imaging) can be covered when the X-ray detector having the size larger than the X-ray detector size (recommended detector size) is chosen. On the other hand, in consideration of the needs to use a small X-ray detector as much as possible, by choosing the smallest-size X-ray detector from the corresponding X-ray detectors having the larger size, the range of the X-ray detector (the range of the inspection region) necessary for the inspection can be covered while the above needs are satisfied.

When the X-ray detector having the same size as the X-ray detector size (recommended detector size) is unusable, the X-ray detector having the size larger than the X-ray detector size (recommended detector size) is unusable, and the X-ray detector having the size smaller than the X-ray detector size (recommended detector size) is usable, the third X-ray detector choosing unit chooses the largest-size X-ray detector from the corresponding X-ray detectors having the smaller size. Consequently, even when the X-ray detector having the same size as the X-ray detector size (recommended detector size) is unusable and the X-ray detector having the size larger than the X-ray detector size (recommended detector size) is unusable, the largest-size X-ray detector is selected from the corresponding X-ray detectors having the smaller size (smaller than the X-ray detector size) as the X-ray detector having the size closest to the X-ray detector size (recommended detector size) necessary for the inspection.

In the case that the priority is manually set by the operator, the X-ray detector is chosen based on the sensitivity of the X-ray detector by way of example. However, the X-ray detector may automatically be chosen based on the sensitivity of the X-ray detector. That is, the inspection order information is sensitivity of the X-ray detector in addition to the X-ray detector size (recommended detector size) described above, the X-ray detector selecting unit selects the X-ray detector based on the X-ray detector size (recommended detector size) among the X-ray detectors detected by the X-ray detector detecting unit, and chooses the X-ray detector having the highest sensitivity from the corresponding X-ray detectors based on the usable X-ray detector. When the X-ray detector is automatically chosen based on the sensitivity of the X-ray detector, the X-ray detector is automatically chosen in the order of "usable X-ray detector"→"X-ray detector size (recommended detector size)"→"sensitivity of X-ray detector"→"X-ray detector having highest sensitivity". Consequently, the usable X-ray detector having the highest sensitivity can be used among the X-ray detectors selected based on the X-ray detector size (recommended detector size), and an X-ray irradiation dose can be reduced with increasing sensitivity, which leads to the reduction of radiation exposure of the test object (patient).

The X-ray device includes a first X-ray detector choosing unit that chooses the corresponding X-ray detector when one usable X-ray detector having the highest sensitivity exists even in the case that the X-ray detector is automatically chosen based on the sensitivity of the X-ray detector.

Even in the case that the X-ray detector is automatically chosen based on the sensitivity of the X-ray detector, when the plurality of usable X-ray detectors exist, the operator manually sets the priority for using the X-ray detector, and the X-ray detectors may automatically be chosen according to the priority. That is, similarly, the X-ray device includes a priority setting unit that sets the priority for using the X-ray detector and a second X-ray detector choosing unit that chooses the X-ray detector according to the priority set by the priority setting unit. This case is useful for the case that the plurality of usable X-ray detectors having the highest sensitivity exist, and the second X-ray detector choosing unit chooses the X-ray detector having the top priority set by the priority setting unit from the plurality of corresponding X-ray detectors.

The X-ray device includes a third X-ray detector choosing unit that performs the above choice when the X-ray detector is automatically chosen based on the sensitivity of the X-ray detector. That is, when the X-ray detector having the same size as the X-ray detector size (recommended detector size) is usable, the third X-ray detector choosing unit chooses the X-ray detector having the same size. On the other hand, when the X-ray detector having the same size as the X-ray detector size (recommended detector size) is unusable and the X-ray detector having the size larger than the X-ray detector size (recommended detector size) is usable, the third X-ray detector choosing unit chooses the smallest-size X-ray detector from the corresponding X-ray detectors having the larger size. The X-ray detector having the highest sensitivity is chosen from the corresponding X-ray detectors based on the usable X-ray detector among the smallest-size X-ray detectors chosen by the third X-ray detector choosing unit. By choosing the smallest-size X-ray detector from the corresponding X-ray detectors having the larger size, the range of the X-ray detector (the range of the inspection region) necessary for the inspection can be covered while the needs to use the small X-ray detector as much as possible are satisfied. By choosing the X-ray detector having the highest sensitivity from the plurality of corresponding X-ray detectors having the same size, the usable X-ray detector having the highest sensitivity can be used while the needs are satisfied, and the X-ray irradiation dose of X-rays can be reduced with increasing sensitivity, which leads to the reduction of the radiation exposure of the test object (patient).

The third X-ray detector choosing unit performs the above choice even when the X-ray detector is automatically selected based on the sensitivity of the X-ray detector. That is, the third X-ray detector choosing unit chooses the largest-size X-ray detector from the corresponding X-ray detectors having the smaller size when the X-ray detector having the same size as the X-ray detector size (recommended detector size) is unusable, the X-ray detector having the size larger than the X-ray detector size (recommended detector size) is unusable, and the X-ray detector having the size smaller than the X-ray detector size (recommended detector size) is usable. The X-ray detector having the highest sensitivity is chosen from the corresponding X-ray detectors based on the usable X-ray detector among the largest-size X-ray detectors chosen by the third X-ray detector choosing unit. Consequently, even when the X-ray detector having the same size as the X-ray detector size (recommended detector size) is unusable and the X-ray detector having the size larger than the X-ray detector size (recommended detector size) is unusable, the largest-size X-ray detector is chosen from the corresponding X-ray detectors having the smaller size (smaller than the X-ray detector size) as the X-ray detector having the size closest to the X-ray detector size (recommended detector size) necessary for the inspection. The usable X-ray detector having the highest sensitivity can be used, and the X-ray irradiation dose can be reduced with increasing sensitivity, which leads to the reduction of the radiation exposure of the test object (patient).

In the X-ray device of the present invention, the selection and the choice are preferentially performed as described below rather than the selection by the X-ray detector selecting unit or the choice of the X-ray detectors based on the usable X-ray detector.

The X-ray device includes a first change setting unit that changes setting of the unusable X-ray detector to the usable state. The X-ray detector changed to the usable state by the first change setting unit is chosen with top priority. For example, in the case that the X-ray detector is shared by the plurality of X-ray devices, by using the X-ray detector in one X-ray device, the X-ray detector becomes unusable in the other X-ray device. In the case that the X-ray detector is used in the other X-ray device, the X-ray detector is chosen with the top priority in the other X-ray device by changing the unusable state to the usable state by the first change setting unit.

The X-ray device includes a second change setting unit that changes setting of the X-ray detector chosen as the usable X-ray detector to the unusable state. When the X-ray detector is set to the unusable state by the second change setting unit, the selection is performed again by the X-ray detector selecting unit among the usable X-ray detectors detected by the X-ray detector detecting unit to choose the X-ray detector again.

For example, among the usable X-ray detectors, one X-ray detector is chosen with top priority. For example, an imaging failure operation or an order duplication operation is performed on the already-inspected inspection order, and new inspection order is added. In this case, when the X-ray detector that is most recently used to perform the re-imaging or the X-ray detector that is the added inspection order target is in a usable state, the X-ray detector may be used by choosing the X-ray detector with the top priority.

A control device that controls the X-ray device of the present invention includes: an X-ray detector detecting unit that detects a usable X-ray detector; and an X-ray detector selecting unit that selects an X-ray detector that is a choice target based on inspection order information. The X-ray detector chosen by the X-ray detector selecting unit is selected among the X-ray detectors detected by the X-ray detector detecting unit.

A control method for controlling the X-ray device of the present invention includes: an X-ray detector detecting step of detecting a usable X-ray detector; and an X-ray detector selecting step of selecting an X-ray detector that is a choice target based on inspection order information. The X-ray detector selected in the X-ray detector selecting step is chosen among the X-ray detectors detected in the X-ray detector detecting step.

A control program causing a computer to execute a series of pieces of processing for controlling the X-ray device of the present invention, the control program includes: an X-ray detector detecting step of detecting a usable X-ray detector; and an X-ray detector selecting step of selecting an X-ray detector that is a choice target based on inspection order information. The X-ray detector selected in the X-ray detector selecting step is chosen among the X-ray detectors detected in the X-ray detector detecting step, and the computer is caused to execute the pieces of processing in these steps.

According to the control device, the control method, and the control program according to the present invention, similarly to the X-ray device according to the present invention as described above, the corresponding X-ray detector is chosen among the usable X-ray detectors (detected by the X-ray detector detecting unit) based on the inspection order information, so that the X-ray detector suitable for the purpose (of the inspection order) can automatically be chosen from the usable X-ray detectors in the case that there is a possibility that the usable X-ray detector can dynamically be changed at the timing of performing the inspection.

Advantageous Effects of Invention

According to the X-ray device of the present invention, the control device and the control method for controlling the X-ray device, and the control program, the corresponding X-ray detector is chosen among the usable X-ray detectors (detected by the X-ray detector detecting unit) based on the inspection order information, so that the X-ray detector suitable for the purpose (of the inspection order) can automatically be chosen from the usable X-ray detectors in the case that there is a possibility that the usable X-ray detector can dynamically be changed at the timing of performing the inspection.

BRIEF DESCRIPTION OF DRAWINGS

FIG. 7 is a block diagram of a console according to another modification.

DESCRIPTION OF EMBODIMENTS

An embodiment of the present invention will be described below with reference to the drawings.

Figure 1:
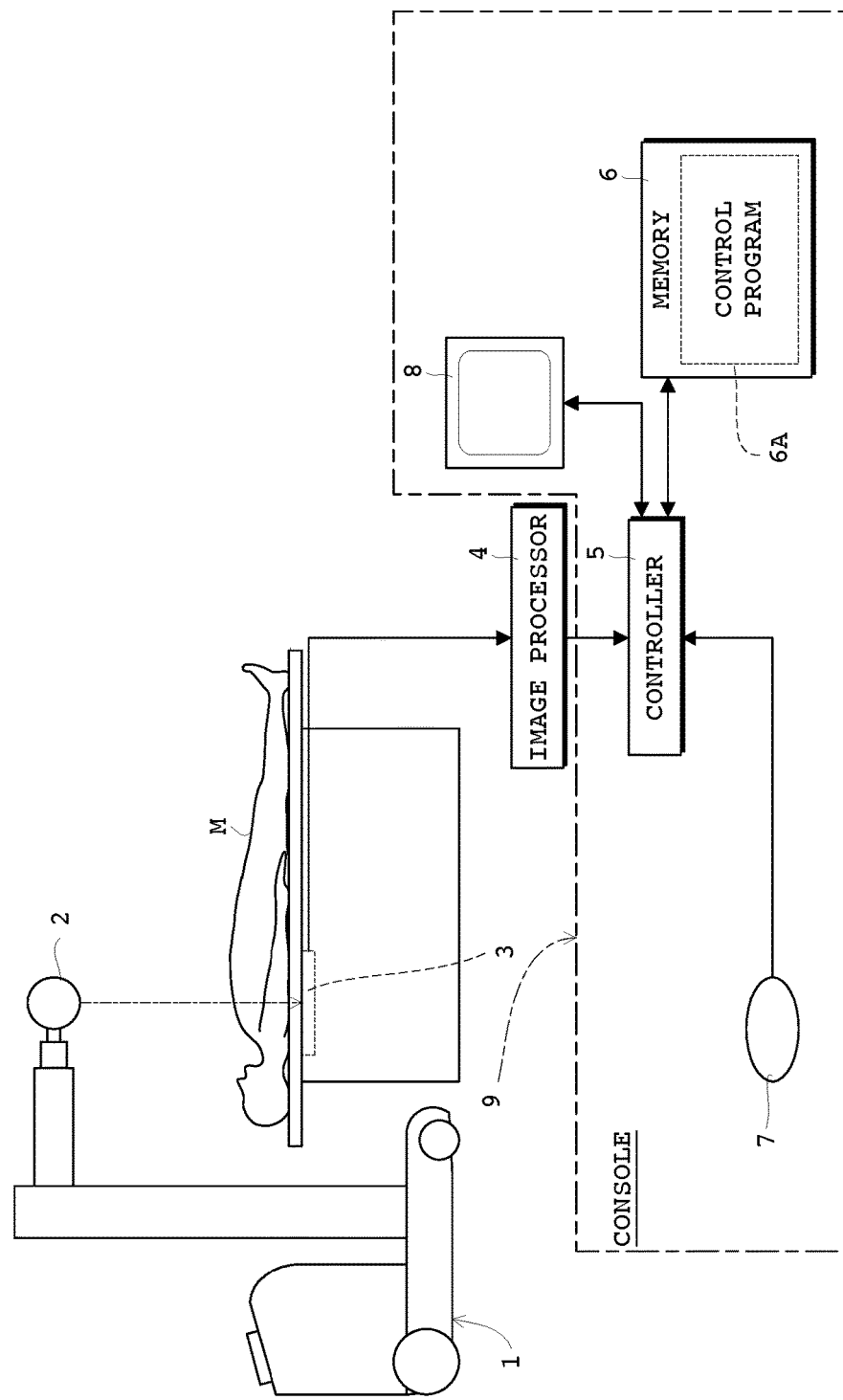
FIG. 1 is a block diagram of an X-ray imaging device according to an embodiment.
Figure 2:
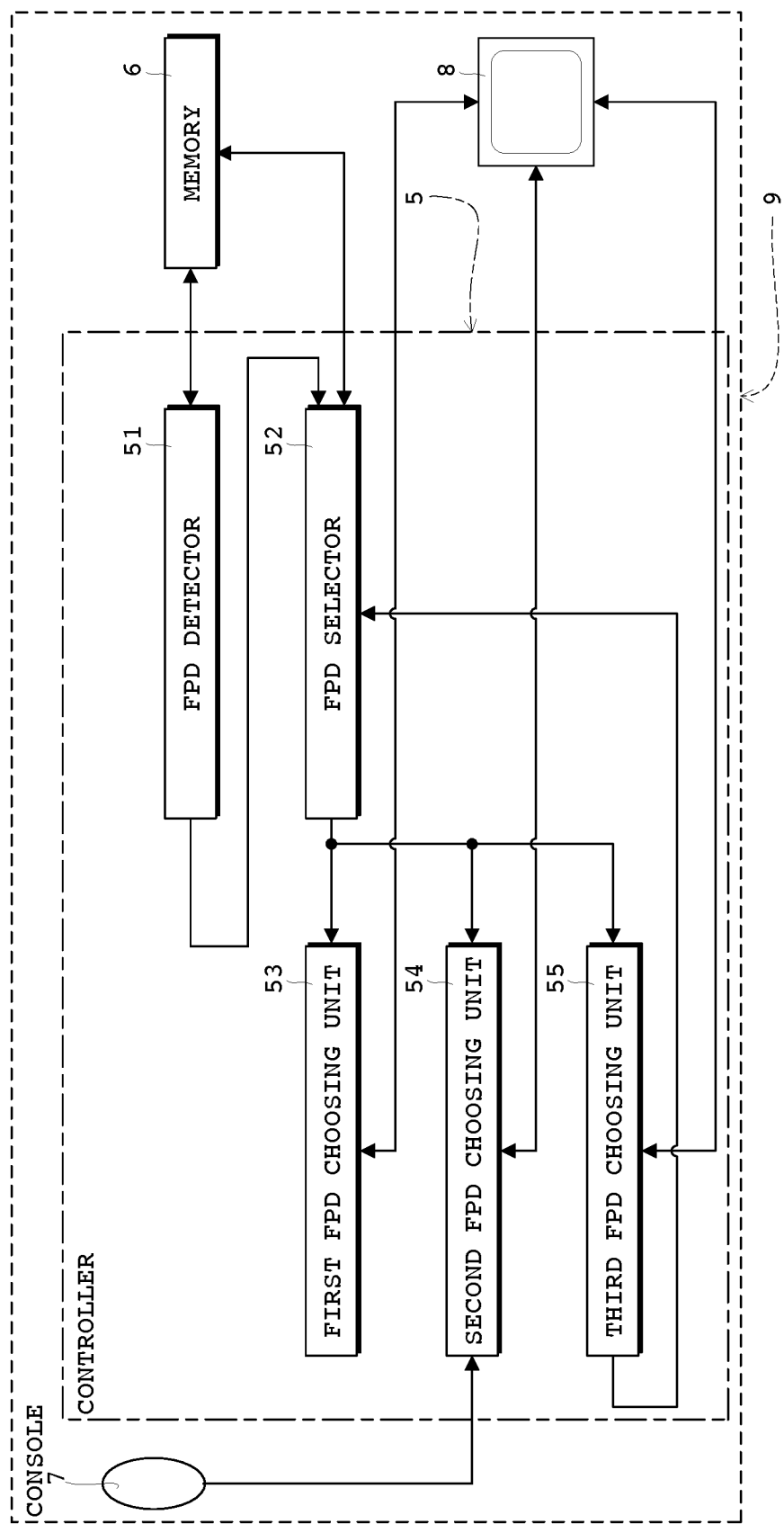
FIG. 2 is a block diagram of a console according to the embodiment.

FIG. 1 is a block diagram of an X-ray imaging device according to an embodiment, and FIG. 2 is a block diagram of a console according to the embodiment. In the embodiment, inspection in an X-ray device will be described by taking imaging as an example, and the X-ray device will be described by taking an X-ray imaging device for round visit including a mobile truck as an example.

As illustrated in FIG. 1, the X-ray imaging device of the embodiment includes a mobile truck 1, an X-ray tube 2 that emits an X-ray toward a test object M that is a patient, and a flat panel X-ray detector (FPD) 3 that detects the X-ray emitted from the X-ray tube 2 and transmitted through the test object M. In FIG. 1, the mobile truck 1 includes a support and a telescopic arm, one end of the telescopic arm holds the X-ray tube 2 and holds the FPD 3 below a top board on which the test object M is placed, whereby the X-ray tube 2 and the FPD 3 are provided to be opposed to each other. The movable truck is not limited to the structure in FIG. 1. Alternatively, the movable truck may have a structure in which a C arm is provided, one end of the C arm holds the X-ray tube, and the other end of the C arm holds the FPD, whereby the X-ray tube and the FPDs are opposed to each other. In the embodiment, because the X-ray imaging device is for round visit, the top board on which the test object M is placed is installed independently of the X-ray imaging device. The X-ray tube 2 corresponds to the X-ray tube of the present invention, and the flat panel X-ray detector (FPD) 3 corresponds to the X-ray detector of the present invention.

Additionally, the X-ray imaging device includes an image processor 4 that performs image processing based on the X-ray detected by the FPD 3, a controller 5 that totally controls each component, and a memory 6 that stores an X-ray image obtained by various kinds of image processing performed by image processor 4 under the control of the controller 5 and stores imaging order information (to be described later), an input unit 7 used to input data and a command by an operator such as a technician, and a display 8 that displays the X-ray image of the image processor 4 and explicitly displays the automatically-chosen FPD 3 (to be described later). The controller 5 corresponds to the control device of the present invention, and the input unit 7 corresponds to the priority setting unit of the present invention.

The controller 5, the memory unit 6, the input unit 7, and the display unit 8 constitute a console 9. The image processor 4 may be included in the console 9. A specific configuration of the console 9 will be described later with reference to FIG. 2.

The FPD 3 is constructed by arranging a plurality of detection elements which are sensitive to the X-ray in a two-dimensional matrix on a detection surface of the FPD 3. The detection element converts the X-ray transmitted through the test object M into an electric signal, temporarily stores the electric signal, and reads the stored electric signal to detect the X-ray. The electric signals detected by each detection element is converted into a pixel value corresponding to the electric signal, and the X-ray image is output by assigning the pixel value to a pixel corresponding to the position of the detection elements. The output X-ray image is sent to the image processor 4 or the memory 6 through the controller 5. As described above, the FPD 3 is used for an X-ray imaging digital device while a plurality of detection elements that detect the X-ray are arranged in a matrix shape (two-dimensional matrix shape). The X-ray detector is not limited to the FPD, but may be an X-ray detector used for an X-ray imaging analog device such as an image intensifier (I.I).

The FPD 3 may be a direct conversion type X-ray detector including a photoelectric conversion layer that directly converts the X-ray into the electric signal or an indirect conversion type X-ray detector that indirectly converts the X-ray into the electric signal while including a scintillator that converts the X-ray into light and a photoelectric conversion layer that converts the converted light into the electric signal. The output of the electric signal with respect to an irradiation dose of the X-ray is proportional to sensitivity of the FPD 3. The sensitivity varies depending on a material constituting the photoelectric conversion layer or the scintillator. In the embodiment, the sensitivity of each FPD 3 is obtained before imaging, and written and stored in the memory 6 as the imaging order information.

In the embodiment, the FPDs 3 having various sensitivities and the FPDs 3 having various recommended detector sizes are prepared, and these FPDs 3 are shared by a plurality of X-ray imaging devices.

The image processor 4 and the controller 5 are constructed with a central processing unit (CPU) or the like. The image processor 4 may be constructed with a GPU (Graphics Processing Unit) or the like.

The memory 6 is constructed with a storage medium typified by a ROM (Read-only Memory) or a RAM (Random-Access Memory). In the embodiment, the X-ray image obtained by the FPD 3 is written and stored after the image processing of the image processor 4, read from the memory 6 as necessary, and sent to the display 8 or a printer (not illustrated). In the embodiment, the imaging order information such as a FPD size (recommended detector size) and the sensitivity of the FPD 3 necessary for inspection is written and stored, read from the memory 6 at the time of selection of the FPD selector 52 of the controller 5 (refer to FIG. 2), and sent to the FPD selector 52. Information about a list of usable detectors (to be described later) is written and stored, and the detector list information is read from the memory 6 and sent to the FPD detector 51 of the controller 5 at the time of detection (listing) of the FPD detector 51.

At this point, an operation to set the FPD 3 usable is previously performed in order to list (detect) the usable FPD 3. Although there is no particular limitation on a technique of setting the FPD 3 usable, the description will be made by taking authentication performed by a communication unit as an example. Specifically, in order to use a detector a, which is usable in a device A, in a device B, communication is conducted between the device B and the detector a using the communication unit, and the detector a is authenticated by the device B to put the detector a into a state in which the detector a belongs to the device B.

For the authentication performed by the communication unit, preferably the authentication is performed using a communication unit different from the communication unit between the device and the detector under a normal condition. For example, when the device and the detector normally communicate with each other by wireless LAN (Local Area Network), the device and the detector is electrically connected to each other using a wired cable, and the authentication is performed such that the detector belongs to the device connected by the wired cable. Conversely, when the communication is conducted between the device and the detector using the wired cable, infrared communication is conducted between the device and the detector by wireless LAN, whereby the detector is authenticated so as to belong to the device of a communication partner. The authenticated detector is written and stored as the detector list information in the memory of the corresponding device.

Typically, a plurality of usable detectors are authenticated. When a plurality of usable detectors are authenticated, the same number of usable detectors as the communication units may simultaneously be authenticated using a plurality of communication units (such as the wired cables), or the individual detector may sequentially be authenticated.

Because it is considered that the authentication operation is not frequently performed, the wired cable for normal communication between the device and the detector or the wired cable for charging the detector may also serves as the cable for the authentication in the case that the usable detectors as many as the wired cables are simultaneously authenticated using a plurality of wired cables.

In the case that the individual detector is sequentially authenticated, an operation to conduct the communication between detector that is an authentication target and the devices to cause the device to authenticate detector, to complete the communication between the authenticated detector and the device when the detectors are authenticated, and to set the next detector as the detector that is the authentication target is sequentially performed on the individual detector. In the case that the communication unit is the wired cable, an operation to conduct the communication between the detector that is the authentication target and the device by electrically connecting the wired cable to the detector that is the authentication target and the device, to cause the device to authenticate the detector, to complete the communication between the authenticated detector and the device by electrically disconnecting the wired cable from the authenticated detector and the device, and to set the next detector as the detector that is the authentication target by electrically connecting the wired cable to the next detector and the device is sequentially performed on the individual detector.

At this point, in the case that the detector is shared by a plurality of devices, the detector is not allowed to be simultaneously authenticated by the plurality of devices in order to prevent the detector that communicates with the device from becoming undiscriminatable. For example, in the case that the detector a is shared by the two devices A, B, the detector a is deleted from the detector list information of the device A to cause the device B to authenticate the detector a when the detector a used by the device A is used in the device B. In this way, the two devices A, B are not allowed to simultaneously authenticate the detector a.

Once the authentication is performed, it is not necessary to perform the reauthentication unless the authentication is canceled for some reason such that, for example, the authentication is performed by another device or the operator deletes the detector information from the detector list information. Thus, even if the power supply of the device is turned off or on, it is not necessary to perform the authentication again.

A registration operation may be performed for each detector prior to the authentication. As used herein, the registration operation means an operation to write and store the information about the detector in the memory of the corresponding device. Only in the case that the detector registered in the device is authenticated, the detector is usable by the device. Conversely, even if the authentication operation is performed for the detector that is not registered in the device, the unregistered detector is unusable by the device. In this way, only the detector in which both the registration operation and the authentication operation are performed for the device may be usable. The registration operation can be previously performed on all devices likely to be used.

The authentication performed by the communication unit is described above by way of example. However, in addition to the authentication performed by the communication unit, it may be set that the detector typified by the FPD 3 can be used as described below. For example, in the case that a wireless detector is moved out of a radio wave range, the wireless detector may be deleted from the usable detector list information even if the wireless detector is already authenticated. On the contrary, the wireless detector located outside the radio wave range is moved into the radio wave range, the wireless detector may automatically be added to the usable detector list information. The detector may be deleted from the usable detector list information by simply turning off the power supply of the detector, and the detector may automatically be added to the usable detector list information by simply turning on the power supply of the detector. That is, the detector is set to be unusable when the detector cannot communicate with the device, and the detector is set to be usable when the detector can communicate with the device.

The input unit 7 is constructed with a pointing device typified by a mouse, a keyboard, a joystick, a trackball, or a touch panel. In the embodiment, in order that the operator manually sets the priority for using the FPD 3, the priority is input based on the imaging order information such as the recommended detector size and the sensitivity of the FPD 3. As described later, in the embodiment, the recommended detector size and sensitivity are already used such that the FPD 3 is selected based on the recommended detector size, and such that the FPD 3 having the highest sensitivity is chosen in the case that the sensitivity is considered. For this reason, the operator may arbitrarily set the priority for using the FPD 3 using the imaging order information except for the recommended detector size and the sensitivity (for example, the size of the test object or a region of interest or an imaging region).

Figure 4:
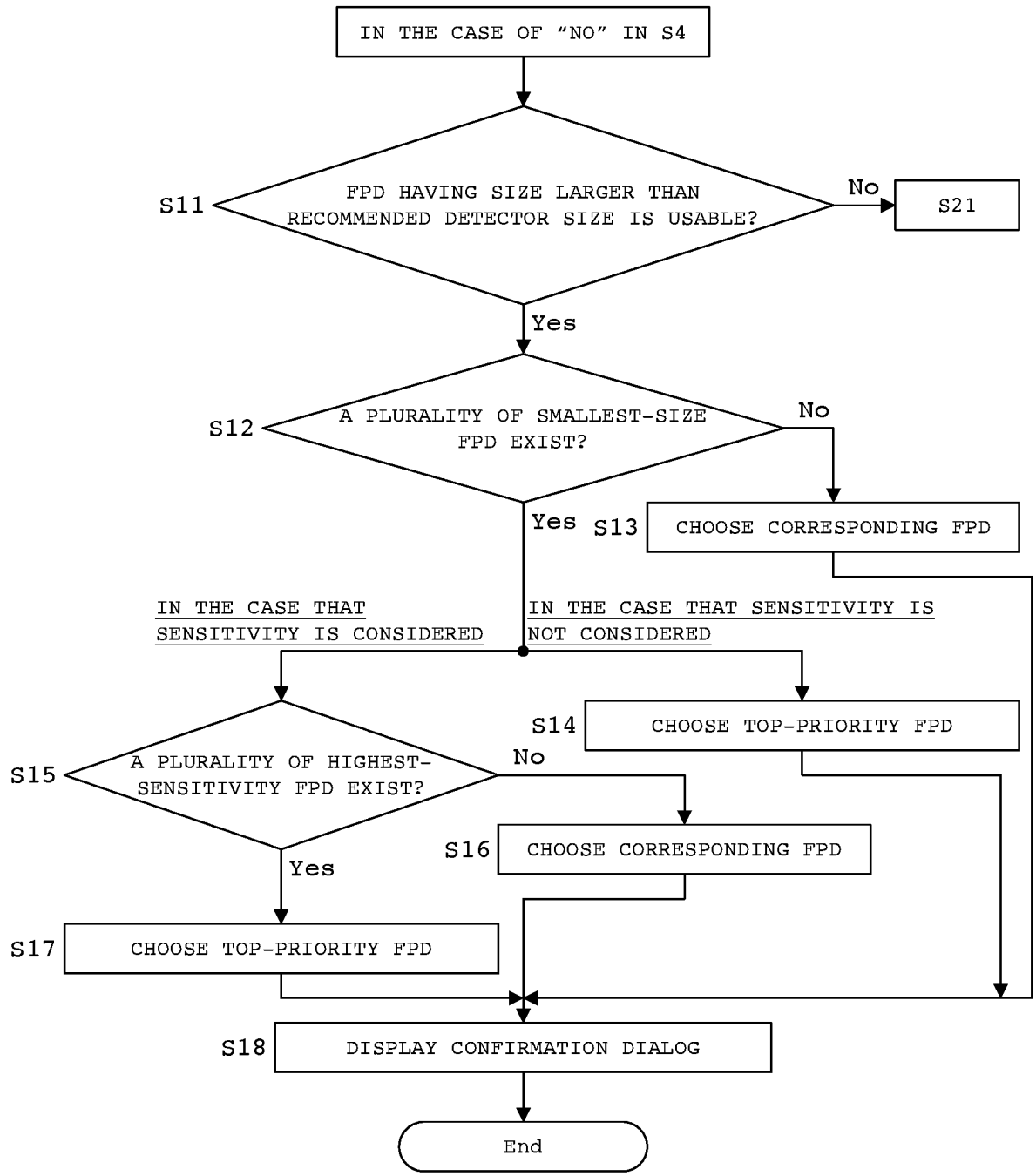
FIG. 4 is a flowchart of the embodiment when the flat panel X-ray detector (FPD) having the same size as the recommended detector size is unusable, and when a flat panel X-ray detector (FPD) having the size larger than the recommended detector size is usable.
Figure 5:
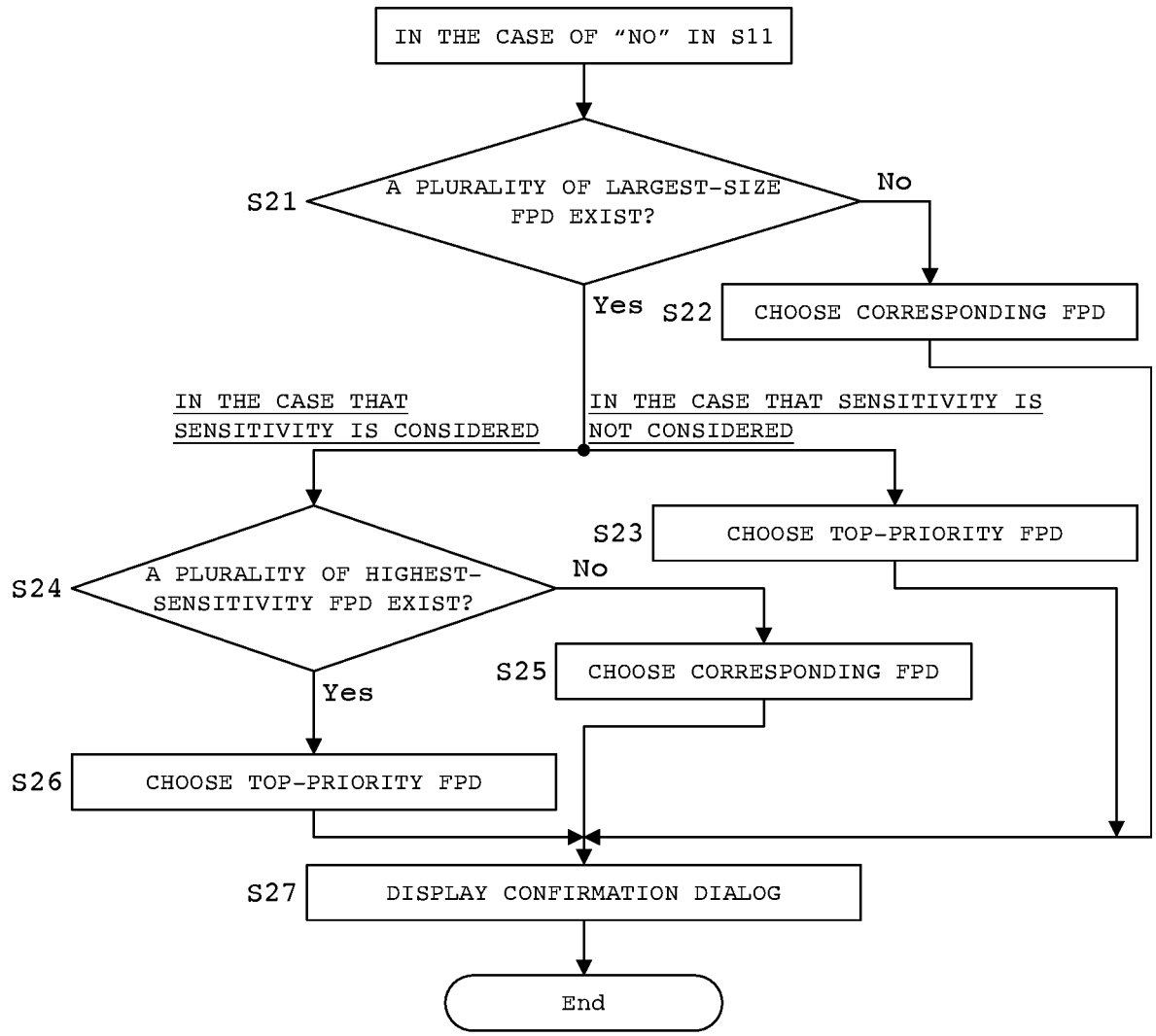
FIG. 5 is a flowchart of the embodiment when the flat panel X-ray detector (FPD) of the same size as the recommended detector size is unusable, when the flat panel X-ray detector (FPD) having the size larger than the recommended detector size is unusable, and when the flat panel X-ray detector (FPD) having the size smaller than the recommended detector size is usable.

The display 8 is constructed with a touch panel, a monitor, a television, and the like. In the embodiment, the FPD 3 chosen by the first to third FPD choosing units 53 to 55 (refer to FIG. 2) of the controller 5 (to be described later) is explicitly displayed on the display 8, and a confirmation dialog is displayed on the display 8 when the FPD 3 having another size different from the recommended detector size is chosen as illustrated in the flowchart of FIG. 4 or FIG. 5 to be described later (refer to step S18 in FIG. 4 or step S27 in FIG. 5).

As illustrated in FIG. 2, the console 9 includes a controller 5, a memory 6, an input unit 7, and a display 8 (also refer to FIG. 1). The controller 5 includes an FPD detector 51, an FPD selector 52, and first to third FPD choosing units 53 to 55. The FPD detector 51 corresponds to the X-ray detector detecting unit of the present invention, the FPD selector 52 corresponds to the X-ray detector selecting unit of the present invention, the first FPD choosing unit 53 corresponds to the first X-ray detector choosing unit of the present invention, the second FPD choosing unit 54 corresponds to the second X-ray detector choosing unit of the present invention, and the third FPD choosing unit 55 corresponds to the third X-ray detector choosing unit of the present invention.

A program (e.g., software or computer executable code) for performing the detection by the FPD detector 51, the selection by the FPD selector 52, and the choice by the first to third FPD choosing units 53 to 55 are written in a storage medium (memory 6) typified by a ROM (e.g., compact disk (CD ROM)), and the CPU (controller 5) of the console 9 reads the program from the storage medium and executes the program, thereby performing the detection by the FPD detector 51, the selection by the FPD selector 52, and the choice by the first to third FPD choosing units 53 to 55 according to the program. The storage medium (memory 6) may be other types of a non-transitory tangible computer readable storage medium other than ROM, such as a hard disk drive, a programmable rewritable nonvolatile memory (e.g., NAND flash memory, PRAM, MRAM, RRAM, etc.), or volatile memory such as DRAM or SRAM. In FIG. 1, a control program 6A is illustrated in the memory 6. The control program 6A corresponds to the control program of the present invention.

The FPD detector 51 detects the usable FPD 3. In the embodiment, the detector list information stored in the memory 6 as the authenticated FPD 3 is read out, and the FPD detector 51 refers to the detector list information to detect the usable FPD 3. The detected FPD 3 is sent to the FPD selector 52.

The FPD selector 52 selects the FPD 3 that is a choice target based on the imaging order information stored in the memory 6. In the embodiment, as described above, the imaging order information is the sensitivity of the FPD 3 in addition to the FPD size (recommended detector size) necessary for the inspection. The FPD selector 52 selects the FPD 3 based on the recommended detector size. In the case that the sensitivity of the FPD 3 is considered, the FPD 3 having the highest sensitivity is selected and chosen from the corresponding FPDs 3. The information about the selected FPD 3 is sent to the first to third FPD choosing units 53 to 55. The switching to the first FPD choosing unit 53 is performed when one usable FPD 3 exists, the switching to the second FPD choosing unit 54 is performed when the plurality of usable FPDs 3 exist, and the switching to the third FPD choosing unit 55 is performed when the FPD 3 having the same size as the recommended detector size is unusable (that is, when the detector having the same size as the recommended detector size does not exist in the detector list information).

Figure 3:
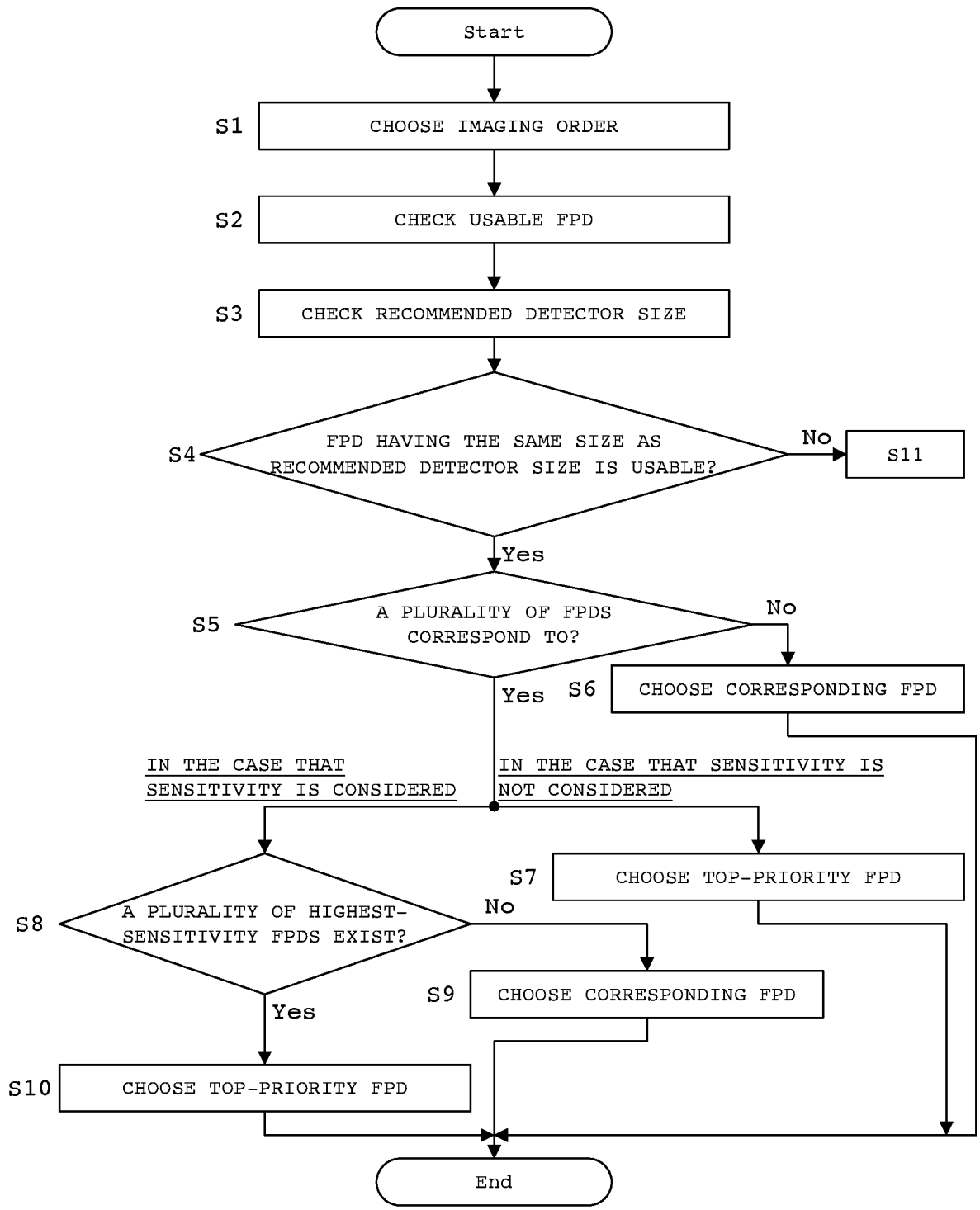
FIG. 3 is a flowchart of the embodiment when a flat panel X-ray detector (FPD) having the same size as a recommended detector size can be used.

When one usable FPD 3 having the same size as the recommended detector size exists, the first FPD choosing unit 53 chooses the corresponding FPD 3 as illustrated in the flowchart of FIG. 3 (refer to step S6 in FIG. 3). In the case that the sensitivity is considered, when one FPD 3 having the highest sensitivity exists among the usable FPDs 3 having the same size as the recommended detector size, the first FPD choosing unit 53 chooses the FPD 3 as illustrated in the flowchart of FIG. 3 (refer to step S9 in FIG. 3).

When the FPD 3 having the same size as the recommended detector size is unusable, when the FPD 3 having the size larger than the recommended detector size is usable, and when one FPD 3 having the smallest size exists among the FPDs 3 having the size larger than the recommended detector size, the first FPD choosing unit 53 chooses the corresponding FPD 3 as illustrated in the flowchart of FIG. 4 (refer to step S13 in FIG. 4). In the case that the sensitivity is considered, when one FPD 3 having the smallest size and the highest sensitivity exists among the FPDs 3 having the size larger than the recommended detector size, the first FPD choosing unit 53 chooses the corresponding FPD 3 as illustrated in the flowchart of FIG. 4 (refer to step S16 in FIG. 4).

When the FPD 3 having the same size as the recommended detector size is unusable, when the FPD 3 having the size larger than the recommended detector size is unusable, when the FPD 3 having the size smaller than the recommended detector size is usable, and when one FPD 3 having the largest size exists among the FPDs 3 having the size smaller than the recommended detector size, the first FPD choosing unit 53 chooses the FPD 3 as illustrated in the flowchart of FIG. 5 (refer to step S22 in FIG. 5). In the case that the sensitivity is considered, when one FPD 3 having the largest size and the highest sensitivity exists among the FPDs 3 having the size smaller than the recommended detector size, the first FPD choosing unit 53 chooses the corresponding FPD 3 as illustrated in the flowchart of FIG. 5 (refer to step S25 in FIG. 5).

When the plurality of usable FPDs 3 having the same size as the recommended detector size exist, the second FPD choosing unit 54 chooses the highest-priority FPD 3 set by the input unit 7 among the plurality of corresponding FPDs 3 as illustrated in the flowchart of FIG. 3 (refer to step S7 or S10 in FIG. 3).

When the FPD 3 having the same size as the recommended detector size is unusable, when the FPD 3 having the size larger than the recommended detector size is usable, and when the plurality of smallest-side FPDs 3 exist among the PFDs 3 having the size larger than the recommended detector size, the second FPD choosing unit 54 chooses the highest-priority FPD 3 set by the input unit 7 from the FPDs 3 as illustrated in the flowchart of FIG. 4 (refer to step S14 or S17 in FIG. 4).

When the FPD 3 having the same size as the recommended detector size is unusable, when the FPD 3 having the size larger than the recommended detector size is unusable, when the FPD 3 having the size smaller than the recommended detector size is usable, and when the plurality of FPDs 3 having the largest size exist among the FPDs 3 having the size smaller than the recommended detector size, the second FPD choosing unit 54 chooses the highest-priority FPD 3 set by the input unit 7 among the FPDs 3 as illustrated in the flowchart of FIG. 5 (refer to step S23 or S26 in FIG. 5).

Unless the FPD 3 having the same size as the recommended detector size is usable, the third FPD choosing unit 55 chooses the FPD 3 as follows. When the FPD 3 having the size larger than the recommended detector size is usable, the third FPD choosing unit 55 chooses the FPD 3 having the smallest size from the corresponding large-sized FPDs 3 as illustrated in the flowchart of FIG. 4 (refer to step S11 in FIG. 4). When the FPD 3 having the size larger than the recommended detector size is unusable and when the FPD 3 having the size smaller than the recommended detector size is usable, the third FPD choosing unit 55 chooses the largest-size FPD 3 is chosen from the corresponding small-size FPD 3 as illustrated in the flowchart of FIG. 5 (refer to step S21 in FIG. 5). In the case that the FPD 3 chosen by the third FPD choosing unit 55 is further selected based on the imaging order information, the FPD 3 chosen by the third FPD choosing unit 55 is sent to the FPD selector 52.

The FPD 3 chosen by the first to third FPD choosing units 53 to 55 is sent to the display 8 in order to explicitly display the FPD 3.

Each flowchart of control relating to the choice will be described below with reference to FIGS. 3 to 5. FIG. 3 is a flowchart of the embodiment when the flat panel X-ray detector (FPD) having the same size as the recommended detector size is usable, FIG. 4 is a flowchart of the embodiment when the flat panel X-ray detector (FPD) having the same size as the recommended detector size is unusable and when the flat panel X-ray detector (FPD) having the size larger than the recommended detector size is usable, and FIG. 5 is a flowchart of the embodiment when the flat panel X-ray detector (FPD) having the same size as the recommended detector size is unusable, when the flat panel X-ray detector (FPD) having the size larger than the recommended detector size is unusable, and when the flat panel X-ray detector (FPD) having the size smaller than the recommended detector size is usable.

The flow charts in FIGS. 3 to 5 are started in such timing that the imaging order of step S1 in FIG. 3 is chosen (that is, the imaging is started based on certain imaging order information), the number of usable FPDs 3 (see FIGS. 1 and 2) increases or decreases, or failure of the imaging or re-imaging is performed. The flowchart in FIG. 3 will be described.

(Step S1) Choosing the Imaging Order

An operator chooses the imaging order information stored in the memory 6 (refer to FIGS. 1 and 2). The chosen imaging order is read from the memory 6, and sent to the FPD selector 52 (refer to FIG. 2).

(Step S2) Checking the Usable FPD

The FPD detector 51 (refer to FIG. 2) refers to the detector list information read from the memory 6, and detects the usable FPD 3. This detection is also called "listing", and the usable FPD 3 is checked by detecting the usable FPD 3. A check result is sent to the FPD selector 52. This step S2 corresponds to the X-ray detector detecting step of the present invention.

(Step S3) Checking the Recommended Detector Size

The recommended detector size associated with the imaging order information chosen in step S1 is checked. Because the imaging order information is the recommended detector size, the FPD selector 52 selects the FPD 3 that matches the recommended detector size. At this point, preferably the usable FPD 3 that does not match the recommended detector size is also selected. This step S3 corresponds to the X-ray detector selecting step of the present invention.

(Step S4) the FPD Having the Same Size as the Recommended Detector Size can be Used?

Whether the FPD 3 having the same size as the recommended detector size is usable is determined. When the FPD 3 having the same size as the recommended detector size is unusable (refer to "No" in FIG. 3), the switching to the third FPD choosing unit 55 is performed (refer to FIG. 2) based on the result in step S3, and the process goes to step S11 in FIG. 4. When the FPD 3 having the same size as the recommended detector size is usable (see "Yes" in FIG. 3), the process goes to step S5.

(Step S5) a Plurality of FPDs Correspond to?

When the FPD 3 having the same size as the recommended detector size is usable, whether the plurality of usable FPDs 3 exist is determined. When one usable FPD 3 exists (refer to "No" in FIG. 3), the switching to the first FPD choosing unit 53 is performed (see FIG. 2), and the process goes to step S6. When the plurality of usable FPDs 3 exist (refer to "Yes" in FIG. 3), the process goes to step S7 or S8.

In the case that the sensitivity of the FPD 3 is not considered, the switching to the second FPD choosing unit 54 is performed (refer to FIG. 2), and the process goes to step S7. When the sensitivity of the FPD 3 is considered, the process goes to step S8. Setting whether the sensitivity is considered is previously performed as setting of the device, and the process goes automatically to a branch destination based on a setting value. Of course, it is also possible to display on the display unit (see FIG. 1 and FIG. 2), For example, buttons of "Sensitivity is considered?" and "Sensitivity is not considered?" are displayed on the display 8 (refer to FIGS. 1 and 2), or buttons of "Yes" and "No" is displayed with respect to the button of "Sensitivity is considered?", and the necessity of consideration of the sensitivity may be chosen by clicking one of these buttons using the pointing device of the input unit 7.

(Step S6) Choosing the Corresponding FPD

When one usable FPD 3 exists, the first FPD choosing unit 53 chooses the corresponding FPD 3. In order to explicitly display the FPD 3 chosen by the first FPD choosing unit 53, the FPD 3 is sent to the display 8, and a series of detector choosing process is ended.

(Step S7) Choosing the FPD Having Top Priority

In the case that the sensitivity of the FPD 3 is not considered, when the plurality of usable FPDs 3 exist, the second FPD choosing unit 54 chooses the FPD 3 having the top priority set by the input unit 7 from the plurality of FPDs 3. In order to explicitly display the FPD 3 chosen by the second FPD choosing unit 54, the FPD 3 is sent to the display 8, and the series of detector choosing process is ended.

(Step S8) the Plurality of FPDs Having the Highest Sensitivity Exist?

When the sensitivity of the FPD 3 is considered and when the plurality of usable FPDs 3 exist, whether the plurality of FPDs 3 having the highest sensitivity among the plurality of FPDs 3 is determined. When one usable FPD 3 having the highest sensitivity (refer to "No" in FIG. 3), the switching to the first FPD choosing unit 53 is performed, and the process goes to step S9. When the plurality of usable FPDs 3 having the highest sensitivity exist (refer to "Yes" in FIG. 3), the switching to the second FPD choosing unit 54 is performed, and the process goes to step S10.

(Step S9) Choosing the Corresponding FPD

When the sensitivity of the FPD 3 is considered, and when one usable FPD 3 having the highest sensitivity exists, the first FPD choosing unit 53 chooses the corresponding FPD 3. In order to explicitly display the FPD 3 chosen by the first FPD choosing unit 53, the FPD 3 is sent to the display 8, and a series of detector choosing process is ended.

(Step S10) Choosing the FPD Having Top Priority

In the case that the sensitivity of the FPD 3 is considered, and when the plurality of usable FPDs 3 having the highest sensitivity exist, the second FPD choosing unit 54 chooses the FPDs 3 having the top priority set by the input unit 7 from the plurality of corresponding FPDs 3. In order to explicitly display the FPD 3 chosen by the second FPD choosing unit 54, the FPD 3 is sent to the display 8, and the series of detector choosing process is ended.

The flowchart in FIG. 4 will be described below. When the FPD 3 having the same size as the recommended detector size is unusable (refer to "No" in step S4 of FIG. 3), the process goes to step S11 in FIG. 4.

(Step S11) the FPD Larger than the Recommended Detector Size can be Used?

Whether the FPD 3 having the size larger than the recommended detector size is usable is determined. When the FPD 3 having the size larger than the recommended detector size is unusable (refer to "No" in FIG. 4), the process proceeds to step S21 in FIG. 5. When the FPD 3 having the size larger than the recommended detector size is usable (refer to "Yes" in FIG. 4), the process goes to step S12.

(Step S12) the Plurality of FPDs Having the Smallest Size Exist?

When the FPD 3 having the size larger than the recommended detector size is usable, whether the plurality of FPDs 3 having the smallest size exist among the corresponding FPDs 3 is determined. In the case that one smallest FPD 3 exists (refer to "No" in FIG. 4), the process goes to step S13. When the plurality of smallest FPDs 3 exists (refer to "Yes" in FIG. 4), the process goes to step S14 or S15.

When the sensitivity of the FPD 3 is not considered, the process goes to step S14. When the sensitivity of the FPD 3 is considered, the process goes to step S15.

(Step S13) Choosing the Corresponding FPD

When one smallest FPD 3 exists, the first FPD choosing unit 53 selects the corresponding FPD 3. At this point, because the FPD 3 having the size different from the recommended detector size is chosen, the process goes to step S18 in order to display the confirmation dialog.

(Step S14) Choosing the FPD Having Top Priority

In the case that the sensitivity of the FPD 3 is not considered, when the plurality of smallest FPDs 3 exist, the second FPD choosing unit 54 chooses the FPD 3 having the top priority set by the input unit 7 from the plurality of corresponding FPDs 3. At this point, because the FPD 3 having the size different from the recommended detector size is chosen, the process goes to step S18 in order to display the confirmation dialog.

(Step S15) the Plurality of FPDs Having the Highest Sensitivity Exist?

In the case that the sensitivity of the FPD 3 is considered, when the plurality of the smallest FPDs 3 exist, whether the plurality of FPDs 3 having the highest sensitivity exist among the plurality of FPDs 3 is determined. When one FPD 3 having the highest sensitivity exists (refer to "No" in FIG. 4), the process goes to step S16. When the plurality of FPDs 3 having the highest sensitivity exist (refer to "Yes" in FIG. 4), the process goes to step S17.

(Step S16) Choosing the Corresponding FPD

In the case that the sensitivity of the FPD 3 is considered, when one FPD 3 having the highest sensitivity exists, the first FPD choosing unit 53 chooses the corresponding FPD 3. At this point, because the FPD 3 having the size different from the recommended detector size is chosen, the process goes to step S18 in order to display the confirmation dialog.

(Step S17) Choosing the FPD Having Top Priority

In the case that the sensitivity of the FPD 3 is considered, when the plurality of FPDs 3 having the highest sensitivity exist, the second FPD choosing unit 54 chooses the highest-priority FPD 3 set by the input unit 7 from the plurality of corresponding FPDs 3. At this point, because the FPD 3 having the size different from the recommended detector size is chosen, the process goes to step S18 in order to display the confirmation dialog.

(Step S18) Displaying the Confirmation Dialog

Because the FPD 3 chosen in step S13, S14, S16, or S17 is the FPD 3 having the size different from the recommended detector size, the confirmation dialog is displayed on the display 8. A display mode of the confirmation dialog is not particularly limited. For example, confirmation dialog "FPD having the recommended detector size is unusable, so that the FPD having another size is chosen. Please confirm the currently chosen FPD." is displayed. After the confirmation dialog is displayed, the series of detector choosing process is ended. The confirmation dialog is not necessarily displayed, but may be displayed or not be displayed.

The flowchart in FIG. 5 will be described below. When the FPD 3 having the size larger than the recommended detector size is unusable ("No" in step S11 of FIG. 4), the process goes to step S21 in FIG. 5.

(Step S21) the Plurality of FPDs Having the Largest Size Exist?

When the FPD 3 having the size smaller than the recommended detector size is usable, whether the plurality of FPDs 3 having the largest size exist among the corresponding FPDs 3 is determined. When one largest FPD 3 exists (refer to "No" in FIG. 5), the process goes to step S22. When the plurality of the largest FPDs 3 (refer to "Yes" in FIG. 5), the process goes to step S23 or S24.

In the case that the sensitivity of the FPD 3 is not considered, the process goes to step S23. In the case that the sensitivity of the FPD 3 is considered, the process goes to step S24.

(Step S22) Choosing the Corresponding FPD

When one largest FPD 3 exists, the first FPD choosing unit 53 chooses the corresponding FPD 3. At this point, because the FPD 3 having the size different from the recommended detector size is chosen, the process goes to step S27 in order to display the confirmation dialog.

(Step S23) Choosing the FPD Having Top Priority

In the case that the sensitivity of the FPD 3 is not considered, when the plurality of the largest FPDs 3 exist, the second FPD choosing unit 54 chooses the highest-priority FPD 3 set by the input unit 7 from the plurality of corresponding FPDs 3. At this point, because the FPD 3 having the size different from the recommended detector size is chosen, the process goes to step S27 in order to display the confirmation dialog.

(Step S24) the Plurality of FPDs Having the Highest Sensitivity Exist?

In the case that the sensitivity of the FPD 3 is considered, when the plurality of the largest FPDs 3 exist, whether the plurality of FPDs 3 having the highest sensitivity exist among the plurality of FPDs 3 is determined. When one FPD 3 having the highest sensitivity exists (refer to "No" in FIG. 5), the process goes to step S25. When the plurality of FPDs 3 having the highest sensitivity exist (refer to "Yes" in FIG. 5), the process goes to step S26.

(Step S25) Choosing the Corresponding FPD

In the case that the sensitivity of the FPD 3 is considered, when one FPD 3 having the highest sensitivity exists, the first FPD choosing unit 53 chooses the corresponding FPD 3. At this point, because the FPD 3 having the size different from the recommended detector size is chosen, the process goes to step S27 in order to display the confirmation dialog.

(Step S26) Choosing the FPD Having Top Priority

In the case that the sensitivity of the FPD 3 is considered, when the plurality of FPDs 3 having the highest sensitivity exist, the second FPD choosing unit 54 chooses the highest-priority FPD 3 set by the input unit 7 from the plurality of corresponding FPDs 3. At this point, because the FPD 3 having the size different from the recommended detector size is chosen, the process goes to step S27 in order to display the confirmation dialog.

(Step S27) Displaying the Confirmation Dialog

Because the FPD 3 chosen in step S22, S23, S25, or S26 is the FPD 3 having the size different from the recommended detector size, the confirmation dialog is displayed on the display 8. As described in step S18 of FIG. 4, the display mode of the confirmation dialog is not particularly limited. After the confirmation dialog is displayed, the series of detector choosing process is ended. As described in step S18 of FIG. 4, the confirmation dialog is not necessarily displayed, but may be displayed or not be displayed.

The X-ray imaging device of the embodiment includes the X-ray detector detecting unit (in the embodiment, the FPD detector 51) that detects the usable X-ray detector (in the embodiment, the FPD 3) and the X-ray detector selecting unit (in the embodiment, the FPD selector 52) that selects the X-ray detector (FPD 3) that is the choice target based on the inspection order information (in the embodiment, the imaging order information). The X-ray detector selecting unit (FPD selector 52) chooses the X-ray detector (FPD 3) among the X-ray detectors (FPDs 3) detected by the X-ray detector detecting unit (FPD detector 51) based on the inspection order information (imaging order information). In this way, the corresponding X-ray detector (FPD 3) is chosen among the usable X-ray detectors (FPDs 3) based on the inspection order information (imaging order information), so that the X-ray detector FPD 3 suitable for the purpose (of the imaging order) can automatically be chosen from the usable X-ray detectors (FPDs 3) in the case that there is a possibility that the usable X-ray detector (FPD 3) is dynamically changed at the timing of performing the inspection (in the embodiment, the imaging) (in the embodiment, the X-ray imaging device for round visit travels by the mobile truck 1 to dynamically change the peripheral X-ray imaging device sharing the FPD 3). Consequently, a burden on the operator can be reduced during the inspection operation (in the embodiment, during the imaging operation).

For example, the following case is considered as the case that the X-ray imaging device for round visit travels by the mobile truck 1 to dynamically change the peripheral X-ray imaging device sharing the X-ray detector (FPD 3). As described above, in the case that a certain X-ray detector (FPD 3) shared and used by the devices A, B exist, the dynamic change is performed as follows when the X-ray detector (FPD 3) is changed from "the state in which the X-ray detector (FPD 3) can be used by the device A" to "the state in which the X-ray detector (FPD 3) can be used by the device B". That is, the number of usable X-ray detectors (FPDs 3) is decreased by deleting the corresponding X-ray detector (FPD 3) from the detector list information in the device A, and the corresponding X-ray detector (FPD 3) is authenticated to increase the number of usable X-ray detectors (FPDs 3) in the device B.

In the embodiment, the inspection order information (imaging order information) is the X-ray detector size (recommended detector size) necessary for the inspection, and the X-ray detector selecting unit (FPD selector 52) selects the X-ray detector (FPD 3) is selected based on the recommended detector size. In the case that the X-ray detector (FPD 3) having the same size as the recommended detector size is usable, the X-ray detector (FPD 3) having the same size as the recommended detector size can be chosen. In particular, as described in step S5 of FIG. 3, when one X-ray detector (FPD 3) having the same size exists, the corresponding X-ray detector (FPD 3) having the same size is chosen as described in step S6.

The X-ray imaging device includes the first X-Ray detector choosing unit (in the embodiment, the first FPD choosing unit 53) that chooses the corresponding X-ray detector (FPD 3) as in step S6 or S9 of FIG. 3, step S13 or S16 of FIG. 4, and step S22 or S25 of FIG. 5 when one usable X-ray detector (FPD 3) exists among the X-ray detectors (FPDs 3) selected by the X-ray detector selecting unit (FPD selector 52) including the X-ray detector (FPD 3) having the recommended detector size or the sizes except for the recommended detector size.

In the embodiment, when the plurality of usable X-ray detectors (FPDs 3) including the X-ray detector (FPD 3) having the recommended detector size or the sizes except for the recommended detector size exist, the operator manually sets the priority for using the X-ray detector (FPD 3), and the X-ray detector (FPD 3) is automatically chosen according to the priority. That is, the X-ray imaging device includes the priority setting unit (in the embodiment, the input unit 7) that sets the priority for using the X-ray detector (FPD 3) and the second X-ray detector choosing unit (in the embodiment, the second FPD choosing unit 54) that chooses the X-ray detector (FPD 3) according to the priority set by the priority setting unit (input unit 7). This case is useful for the case that the plurality of usable X-ray detectors (FPDs 3) including the X-ray detector (FPD 3) having the recommended detector size or the sizes except for the recommended detector size exist among the usable X-ray detectors (FPDs 3) detected by the X-ray detector detecting unit (FPD detector 51), and the second X-ray detector choosing unit (second FPD choosing unit 54) chooses the highest-priority X-ray detectors (FPD 3) set by the priority setting unit (input unit 7) from the plurality of X-ray detectors (FPDs 3) as in steps S7 or S10 of FIG. 3, step S14 or S17 of FIG. 4, and step S23 or S26 of FIG. 5.

When the inspection order information (imaging order information) is the recommended detector size as in the embodiment, when the X-ray detector (FPD 3) having same size as the recommended detector size is usable, and when the plurality of X-ray detectors (FPDs 3) having the same size as the recommended detector size exist as described in the step S5 of FIG. 3, the X-ray detector (FPD 3) having the top priority is chosen from the plurality of X-ray detectors (FPDs 3) having same size as the recommended detector size as in step S7 or S10.

The X-ray imaging device includes the third X-ray detector choosing unit (in the embodiment, the third FPD choosing unit 55) that performs the above choice when the inspection order information (imaging order information) is the recommended detector size as in the embodiment. That is, when the X-ray detector (FPD 3) having the same size as the recommended detector size is usable (refer to "Yes" in step S4 of FIG. 3), the third X-ray detector choosing unit (third FPD choosing unit 55) chooses the X-ray detector (FPD 3) having the same size as the recommended detector size. On the other hand, when X-ray detector (FPD 3) having the same size as the recommended detector size is unusable (refer to "No" in step S4 of FIG. 3) and when the X-ray detector (FPD 3) having the size larger than the recommended detector size is usable (refer to "Yes" in step S11 of FIG. 4), the third X-ray detector choosing unit (third FPD choosing unit 55) chooses X-ray detector (FPD 3) having the smallest size from the corresponding X-ray detectors (FPDs 3) having the larger size. When the X-ray detector (FPD 3) having the same size as the recommended detector size is unusable and when the X-ray detector (FPD 3) having the size larger than the recommended detector size is usable, as described also in "Technical Problem" and "Solution to Problem", the range (the range of the region of the imaging region) of the X-ray detector (FPD 3) necessary for the inspection (in the embodiment, the imaging) can be covered when the X-ray detector (FPD 3) having the size larger than the recommended detector size is chosen. On the other hand, in consideration of the need to use a small X-ray detector as much as possible, by choosing the smallest-size X-ray detector (FPD 3) from the corresponding large-size X-ray detectors (FPDs 3), the range of the X-ray detector (the range of the region of the imaging region) necessary for the inspection (imaging) can be covered while the above needs are satisfied.

When the X-ray detector (FPD 3) having the same size as the recommended detector size is unusable (refer to "No" in step S4 of FIG. 3), when the X-ray detector (FPD 3) having the size larger than the recommended detector size is unusable (refer to "No" in step S11 of FIG. 4), and when the X-ray detector (FPD 3) having the size smaller than the recommended detector size is usable, the third X-ray detector choosing unit (third FPD choosing unit 55) chooses the largest-size X-ray detector (FPD 3) from the corresponding small-size X-ray detectors (FPDs 3). Consequently, when the X-ray detector (FPD 3) having the same size as the recommended detector size is unusable and when the X-ray detector (FPD 3) having the size larger than the recommended detector size is unusable, the largest-size X-ray detector (FPD 3) is chosen from the corresponding X-ray detectors (FPDs 3) having the small size (smaller than the recommended detector size) as the X-ray detector (FPD 3) having the size closest to the X-ray detector size (recommended detector size) necessary for the inspection.

In the embodiment, the inspection order information (imaging order information) is the sensitivity of the X-ray detector (FPD 3) in addition to the recommended detector size, and the X-ray detector detecting unit (FPD selector 52) among the X-ray detectors (FPDs 3) detected by the X-ray detector detecting unit (FPD detector 51) selects the X-ray detector (FPD 3) based on the recommended detector size, and chooses the X-ray detector (FPD 3) having the highest sensitivity from the corresponding X-ray detectors (FPDs 3) based on the usable X-ray detector (FPD 3). When the X-ray detector (FPD 3) is automatically chosen based on the sensitivity of the X-ray detector (FPD 3) as in the embodiment, the X-ray detector (FPD 3) is automatically chosen in the order of "usable FPD 3"→"recommended detector size"→"sensitivity of FPD 3"→"highest-sensitivity FPD 3". Consequently, the usable X-ray detector (FPD 3) having the highest sensitivity can be used among the X-ray detectors (FPDs 3) selected based on the recommended detector size, and an X-ray irradiation dose can be reduced with increasing sensitivity, which leads to the reduction of radiation exposure of the test object (patient).

When the X-ray detector (FPD 3) is automatically chosen based on the sensitivity of the X-ray detector (FPD 3) and when one X-ray detector (FPD 3) having the highest sensitivity exists among the X-ray detectors (FPDs 3) including the X-ray detectors (FPDs 3) having the recommended detector size or the sizes except for the recommended detector size, the first X-ray detector choosing unit (first FPD choosing unit 53) chooses the corresponding X-ray detector (FPD 3) as in step S9 of FIG. 3, step S16 of FIG. 4, and step S25 of FIG. 5.

When the X-ray detector (FPD 3) is automatically chosen based on the sensitivity of the X-ray detector (FPD 3) and when the plurality of usable X-ray detectors (FPDs 3) having the highest sensitivity exist among the X-ray detectors (FPDs 3) including the X-ray detectors (FPDs 3) having the recommended detector size or the sizes except for the recommended detector size, as described above, the operator manually sets the priority for using the X-ray detector (FPD 3) and the X-ray detector (FPD 3) is automatically chosen according to the priority. That is, similarly, the priority setting unit (input unit 7) sets the priority for using the X-ray detector (FPD 3), and the second X-ray detector choosing unit (second FPD choosing unit 54) chooses the X-ray detector (FPD 3) according to the priority set by the priority setting unit (input unit 7). This case is useful for the case that the plurality of usable X-ray detectors (FPDs 3) having the highest sensitivity exist as in step S8 of FIG. 3, step S15 of FIG. 4, or step S24 of FIG. 5, the second X-ray detector choosing unit (second FPD choosing unit 54) chooses the highest-priority X-ray detector (FPD 3) set by the priority setting unit (input unit 7) from the plurality of corresponding X-ray detectors (FPDs 3) as in step S10 of FIG. 3, step S17 of FIG. 4 and step S26 of FIG. 5.

When the X-ray detector (FPD 3) is automatically chosen based on the sensitivity of the X-ray detector (FPD 3), the third X-ray detector choosing unit (third FPD choosing unit 55) performs the above choice. That is, when the X-ray detector (FPD 3) having the same size as the recommended detector size is usable (refer to "Yes" in step S4 of FIG. 3), the third X-ray detector choosing unit (third FPD choosing unit 55) chooses the X-ray detector (FPD 3) having the same size as the recommended detector size. On the other hand, when X-ray detector (FPD 3) having the same size as the recommended detector size is unusable (refer to "No" in step S4 of FIG. 3) and when the X-ray detector (FPD 3) having the size larger than the recommended detector size is usable (refer to "Yes" in step S11 of FIG. 4), the third X-ray detector choosing unit (third FPD choosing unit 55) chooses X-ray detector (FPD 3) having the smallest size from the corresponding X-ray detectors (FPDs 3) having the larger size. The X-ray detector (FPD 3) having the highest sensitivity is chosen from the corresponding X-ray detectors (FPDs 3) based on the usable X-ray detector (FPD 3) among the smallest-size X-ray detectors (FPDs 3) chosen by the third X-ray detector choosing unit (third FPD choosing unit 55). By choosing the smallest-size X-ray detector (FPD 3) from the corresponding large-size X-ray detectors (FPDs 3), the range of the X-ray detector (the range of the region of the imaging region) necessary for the inspection can be covered while the needs to use the small X-ray detector as much as possible are satisfied. By choosing the X-ray detector (FPD 3) having the highest sensitivity from the plurality of corresponding X-ray detectors (FPD 3) having the same size, the usable X-ray detector (FPD 3) having the highest sensitivity can be used while the needs are satisfied, and the X-ray irradiation dose of X-rays can be reduced with increasing sensitivity, which leads to the reduction of the radiation exposure of the test object (patient).

When the X-ray detector (FPD 3) is automatically chosen based on the sensitivity of the X-ray detector (FPD 3), the third X-ray detector choosing unit (third FPD choosing unit 55) performs the above choice. That is, when the X-ray detector (FPD 3) having the same size as the recommended detector size is unusable (refer to "No" in step S4 of FIG. 3), when the X-ray detector (FPD 3) having the size larger than the recommended detector size is unusable (refer to "No" in step S11 of FIG. 4), and when the X-ray detector (FPD 3) having the size smaller than the recommended detector size is usable, The third X-ray detector choosing unit (third FPD choosing unit 55) chooses the largest-size X-ray detector (FPD 3) from the corresponding small-size X-ray detectors (FPDs 3). The X-ray detector (FPD 3) having the highest sensitivity is chosen from the corresponding X-ray detectors (FPDs 3) based on the usable X-ray detector (FPD 3) among the largest-size X-ray detectors (FPDs 3) chosen by the third X-ray detector choosing unit (third FPD choosing unit 55). Consequently, when the X-ray detector (FPD 3) having the same size as the recommended detector size is unusable and when the X-ray detector (FPD 3) having the size larger than the recommended detector size is unusable, the largest-size X-ray detector (FPD 3) is chosen from the corresponding X-ray detectors (FPDs 3) having the small size (smaller than the recommended detector size) as the X-ray detector (FPD 3) having the size closest to the X-ray detector size (recommended detector size) necessary for the inspection. The usable X-ray detector (FPD 3) having the highest sensitivity can be used, and the X-ray irradiation dose can be reduced with increasing sensitivity, which leads to the reduction of the radiation exposure of the test object (patient).

In the embodiment, by applying the present invention to the X-ray imaging device for round visit including the mobile truck, the X-ray detector (FPD 3) suitable for the purpose (of the imaging order) can automatically be chosen from the usable X-ray detectors (FPDs 3) even if the X-ray imaging device for round visit is moved by the mobile truck 1 to dynamically change the peripheral X-ray imaging device sharing the FPD 3.

In the X-ray imaging device for round visit, unlike the typical imaging device, the imaging is not performed while the X-ray detector (FPD 3) is incorporated in a Bucky device. When the image is performed while the X-ray detector (FPD 3) is incorporated in the Bucky device, the X-ray detector (FPD 3) in the Bucky device may automatically be chosen as the X-ray detector (FPD 3) used in the imaging. Otherwise (in the case that the imaging is performed while the X-ray imaging device for round visit is used as in the embodiment), it is necessary to assign the X-ray detector (FPD 3) used in the imaging in some way. For this reason, in the X-ray imaging device for circular visit, frequently it is necessary to choose the X-ray detector (FPD 3) used in the imaging as compared with the imaging using the typical imaging device. Even if the X-ray detector (FPD 3) in the Bucky device is willfully chosen in the case that the imaging (Bucky imaging) while the X-ray detector (FPD 3) is incorporated in the Bucky device, although there is a low possibility of an improper choice result, it is necessary to choose the X-ray detector (FPD 3) using another piece of information when there is no definitive information selecting the detector such as the Bucky device. Additionally, in the embodiment, because the imaging is performed using the usable X-ray detector (FPD 3) under the condition that is not always the same, there is a high possibility of the improper selection result even if the X-ray detector (FPD 3) is selected in some way. To summarize the above, in the case that the imaging is performed while the X-ray detector (FPD 3) is incorporated in the Bucky device, the possibility of improperly choosing the X-ray detector (FPD 3) is low by restriction of the X-ray detector (FPD 3) used in the imaging. On the other hand, in the case that the imaging is performed while the X-ray detector (FPD 3) is not incorporated in the Bucky device as typified by the X-ray imaging device for round visit, the possibility of improperly choosing the X-ray detector (FPD 3) is high by no restriction of the X-ray detector (FPD 3) used in the imaging.

In the embodiment, even in a situation without the restriction, the X-ray detector (FPD 3) suitable for the purpose (of the imaging order) can automatically be chosen from the usable X-ray detectors (FPDs 3) by applying the present invention to the X-ray imaging device for round visit including a movable truck. As described above, the present invention is useful for the X-ray imaging device for round visit as in the embodiment.

In the embodiment, the same X-ray detector (FPD 3) is shared by the plurality of X-ray imaging devices for round visit. However, the peripheral X-ray imaging device sharing the X-ray detector (FPD 3) may dynamically be changed unless the imaging is performed while the X-ray imaging device (FPD 3) is incorporated in the Bucky device. For example, the peripheral X-ray imaging device sharing the X-ray detector (FPD 3) may dynamically be changed in cases that the same X-ray detector (FPD 3) is shared by the X-ray imaging device for round visit and the stationary X-ray imaging device, and in the case that the same X-ray detector (FPD 3) is shared by the plurality of stationary X-ray imaging devices. However, the case that the X-ray imaging device for round visit moves as in the embodiment to dynamically change the peripheral X-ray imaging device sharing the X-ray detector (FPD 3) may notably be generated For example, although the communication setting of the device and the X-ray detector (FPD 3) remains in "communication enabling setting", as a result of separating the distance from the X-ray detector (FPD 3) by the movement of the device, the radio wave cannot be detected, and the X-ray detector (FPD 3) is not regarded as the usable X-ray detector (FPD 3). Even if such a case occurs, the X-ray detector (FPD 3) suitable for the purpose (of the imaging order) can automatically be chosen from the usable X-ray detectors (FPDs 3) irrespective of the radio wave receiving situation or the like.

In the embodiment, the method for changing the setting to the unusable setting explicitly by the operator (in the embodiment, the authentication operation) is cited as the method for putting the usable X-ray detector (FPD 3) into the state in which the usable X-ray detector (FPD 3) is unusable. However, the present invention is not limited this method. As described in the authentication operation of the embodiment, when the X-ray detector is the wireless type, for example, by moving the usable X-ray detector (FPD 3) out of the radio wave range, the usable X-ray detector (FPD 3) may be handled as the unusable X-ray detector (FPD 3) with "communication cannot be conducted" as a trigger. In the case that such an operation is performed, on the contrary, the unusable X-ray detector (FPD 3) may be handled as the usable X-ray detector (FPD 3) with "the distance between the device and the X-ray detector (FPD 3) is shortened to be able to detect the radio wave" as a trigger.

However, in consideration of the case that which device the X-ray detector (FPD 3) is associated with is unclear as long as the X-ray detector (FPD 3) operates wirelessly, preferably the X-ray detector (FPD 3) is not set to be usable only by the condition that "the device and the X-ray detector are located in the distance where the radio wave can be detected. That is, on the assumption that the X-ray detector (FPD 3) is associated with a certain device, the distance between the device and X-ray detector (FPD 3) is used as a trigger, and the X-ray detector (FPD 3) is usable or unusable from the viewpoint of the device. For example, when the device A is associated with the detector a and when the device A moved away from the detector a while the device B that is not associated with the detector a exists in the vicinity of the detector a, the device A may regard the detector a as the unusable detector. However, the detector a is not connected to the device B, but the detector a continues to keep trying to be connected to the device A. That is, the detector a remains in the unusable state from the viewpoint of the device B which is not associated. Then, when the device A is moved so as to be brought close to the detector a, the device A regards the detector a as the usable detector. In this way, when the distance between the device and the X-ray detector (FPD 3) is used as the trigger, the X-ray detector (FPD 3) may be set to be usable when the device and the X-ray detector (FPD 3) are separated from each other, but only the device associated with the X-ray detector (FPD 3) is set to be usable when the device and the X-ray detector (FPD 3) come close to each other.

The control method of the embodiment includes the X-ray detector detecting step (step S2) of detecting the usable X-ray detector (FPD 3) and the X-ray detector selecting step (step S3) of choosing the X-ray detector (FPD 3) that is the choice target based on the inspection order information (imaging order information), and the X-ray detector (FPD 3) chosen in the X-ray detector selecting step (step S3) is chosen among the X-ray detectors (FPDs 3) detected in the X-ray detector detecting step (step S2).

The control program 6A of FIG. 1 includes the X-ray detector detecting step (step S2) of detecting the usable X-ray detector (FPD 3) and the X-ray detector selecting step (step S3) of choosing the X-ray detector (FPD 3) that is the choice target based on the inspection order information (imaging order information), the X-ray detector (FPD 3) chosen in the X-ray detector selecting step (step S3) is chosen among the X-ray detectors (FPDs 3) detected in the X-ray detector detecting step (step S2), and the pieces of processing in these steps are executed by a computer (in the embodiment, the CPU of the controller 5).

According to the controller 5, the control method, and the control program 6A of the embodiment, similarly to the X-ray imaging device of the embodiment, the corresponding X-ray detector (FPD 3) is chosen among the usable X-ray detectors (FPDs 3) (detected by the FPD detector 51) based on the inspection order information (imaging order information), so that the X-ray detector (FPD 3) suitable for the purpose (of the imaging order) can automatically be chosen from the usable X-ray detectors (FPDs 3) when the usable X-ray detector (FPD 3) may dynamically be changed at the timing of performing the inspection (imaging).

The present invention is not limited to the above embodiment, but can be modified as follows.

(1) In the embodiment, the imaging is described by taking the inspection in the X-ray device as an example. Alternatively, the present invention may be applied to fluoroscopy in which the X-ray image is displayed in real time while the test object is irradiated with the X-ray having the dose weaker than that of the imaging. The present invention may be applied to tomographic imaging such as tomosynthesis and X-ray CT (Computed Tomography) or long imaging for acquiring an elongated image by connecting X-ray images in the longitudinal direction of the test object.

(2) In the embodiment, the X-ray device is described by taking the X-ray imaging device for round visit including the mobile truck as an example. Alternatively, a stationary X-ray device may be used. Examples of the stationary type X-ray device include an X-ray device which is fixedly installed on a floor surface or a ceiling surface to inspect the test object in a supine position and an X-ray device fixedly installed on a wall surface to inspect the test object in a standing posture.

(3) The combination of the X-ray devices sharing the X-ray detector is not particularly limited. The X-ray devices for round visit may be combined as in the embodiment, the X-ray device for round visit and the stationary X-ray device may be combined, or the stationary X-ray devices may be combined.

(4) In the embodiment, the flat panel X-ray detector (FPD), which is the digital X-ray detector capable of communicating with the console, is used as the X-ray detector. However, the kind of the X-ray detector is not particularly limited. The analog X-ray detector may be used as exemplified in the image intensifier (I.I.) and the X-ray film.

(5) In the embodiment, the inspection order information (in the embodiment, the imaging order information) is the recommended detector size and the sensitivity of the X-ray detector (in the embodiment, the FPD 3), and the X-ray detector selecting unit (in the embodiment, FPD selector 52) selects the X-ray detector (FPD 3) based on the recommended detector size. However, the inspection order information (imaging order information) is not limited to the recommended detector size and the sensitivity of the X-ray detector (FPD 3). For example, the inspection order information (imaging order information) may be the size of the test object or the region of interest or the imaging region. In the case that the imaging region is rich in variety such as limbs and a chest, an X-ray detectors for limb imaging associated with the limbs and an X-ray detectors for chest imaging associated with the chest are prepared, and the X-ray detector may be selected based on the chosen imaging region. As disclosed in Patent Literature 2, when the inspection order information (imaging order information) is spatial resolution, an X-ray detector associated with each spatial resolution is prepared, an X-ray detector having the low spatial resolution is selected in the case of the fluoroscopy that does not require the high spatial resolution, and an X-ray detector having the high spatial resolution is selected in the case of the imaging requiring the high spatial resolution.

(6) In the embodiment, the priority is set based on the imaging order information other than the recommended detector size and the sensitivity (for example, the size of the test object or the region of interest or the imaging region). Alternatively, the priority may be set based on the individual recommended detector size or the sensitivity. When the priority is set based on the sensitivity, the X-ray detector having the highest sensitivity is set to the top priority, and the X-ray detector is set to the lower priority with decreasing sensitivity. Consequently, the X-ray detector having high sensitivity can preferentially be used from the usable X-ray detectors, and the X-ray irradiation dose can be reduced with increasing sensitivity, which leads to the reduction of the radiation exposure of the test object (patient). Particularly, this case is useful for the case that the plurality of usable X-ray detectors having the same size exist and the case that the X-ray detector having the top priority is chosen among the plurality of corresponding X-ray detectors having the same size, and the X-ray detector is chosen in the order of "usable X-ray detector"→"X-ray detector size (recommended detector size)"→"sensitivity of X-ray detector-"→"priority" when the priority is set based on the sensitivity.

(7) In the embodiment, the selection by the X-ray detector selecting unit (in the embodiment, the FPD selector 52) and the choice of the X-ray detector (in the embodiment, the FPD 3) based on the usable X-ray detector (in the embodiment, the FPD 3) are preferentially performed. Alternatively, the selection and the choice may preferentially be performed as in the following modifications (8) to (10) rather than the selection by the X-ray detector selecting unit and the choice of the X-ray detector.

Figure 6:
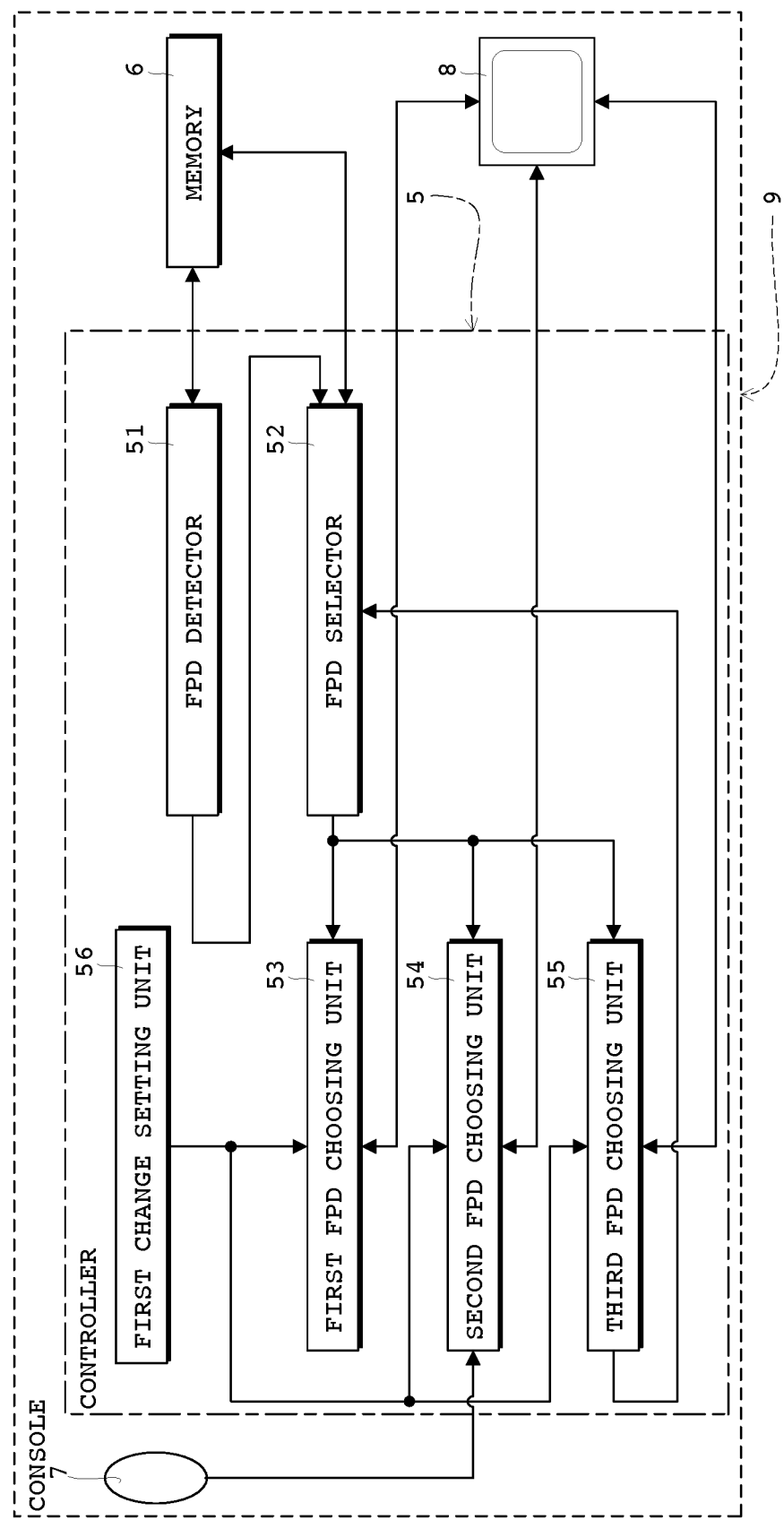
FIG. 6 is a block diagram of a console according to a modification.

(8) For example, the console 9 includes a first change setting unit that changes the setting of the unusable X-ray detector to the usable state. The first change setting unit (the first change setting unit 56 in FIG. 6) is constructed with a communication port of a communication unit that performs the authentication operation described in the above embodiment and a CPU. As described in the authentication operation in the embodiment, the X-ray detector changed to the usable state by the first change setting unit (first change setting unit 56) is chosen the top priority. For example, in the case that the X-ray detector is shared by the plurality of X-ray devices, using the X-ray detector in one X-ray device (device A), the X-ray detector becomes unusable in the other X-ray device (device B). In the case that the X-ray detector is used in the other X-ray device (device B), the X-ray detector is chosen the top priority in the other X-ray device (device B) by changing the unusable state to the usable state by the first change setting unit (first change setting unit 56). Thus, in FIG. 6, the first change setting unit 56 is connected to the first to third FPD choosing units 53 to 55, and the first to third FPD choosing units 53 to 55 do not choose the X-ray detector when the first change setting unit (first change setting unit 56) changes the X-ray detector to be usable state, and the X-ray detector changed to the usable state by the first change setting means (first change setting section 56) is automatically chosen the top priority. The timing of the authentication operation may not be prior to the inspection unlike the embodiment. For example, the authentication operation can be performed during the inspection. That is, the authenticated X-ray detector can automatically be chosen the top priority by interpreting the authenticate of the X-ray detector that is unusable with respect to the device at the timing of the inspection as the immediate use of the X-ray detector in the device.

(9) Conversely, the console 9 may include a second change setting unit that changes the setting of the X-ray detector chosen as the usable X-ray detector to the unusable state. The second change setting unit is constructed with the input unit 7 as illustrated in FIG. 7. When the second change setting unit (input section 7) is set to the unusable state, the selection is performed again by the X-ray detector selecting unit (in FIG. 7, the FPD selector 52) to select the X-ray detector again. For this reason, in FIG. 7, the input unit 7 is connected to the FPD selector 52 and the first to third FPD choosing units 53 to 55, and the selection is performed again by performing the selection by the FPD selector 52 and the choice of the X-ray detector by the first to third FPD choosing units 53 to 55 again when the X-ray detector is changed to the unusable state by the second change setting unit (input unit 7). The second change setting unit may not be the input unit 7. For example, as described in the authentication operation of the embodiment, when the X-ray detector is the wireless type, and when the usable X-ray detector is moved out of the radio wave range, the X-ray detector is deleted from the usable detector list information even if the X-ray detector is already authenticated, whereby the X-ray detector chosen as the usable X-ray detector may automatically be changed to the unusable state. In this case, the second change setting unit is constructed with the communication port of the wireless LAN and the CPU.

(10) For example, among the usable X-ray detectors, one X-ray detector is chosen with top priority. For example, an imaging failure operation or an order duplication operation is performed on the already-inspected inspection order, and new inspection order is added. In this case, when the X-ray detector that is most recently used to perform the re-imaging or the X-ray detector that is the added inspection order target is in a usable state, the X-ray detector may be used by choosing the X-ray detector with the top priority. Any X-ray detector chosen the top priority may be used as long as the X-ray detector is in the usable state, and the operator can choose any one of the usable X-ray detectors the top priority.

(11) In the embodiment, the console 9 includes the first X-ray detector choosing unit (in the embodiment, the first FPD choosing unit 53) that chooses the corresponding X-ray detector when one usable X-ray detector (FPD 3) exists among the X-ray detectors (in the embodiment, the FPD 3) selected by the X-ray detector selecting unit (in the embodiment, the FPD selector 52). Alternatively, the console 9 may include the second X-ray detector choosing unit (in the embodiment, the second FPD choosing unit 54 in the embodiment) without including the first X-ray detector choosing unit (first FPD choosing unit 53) when the plurality of usable X-ray detectors (FPDs 3) exist.

(12) In the embodiment, the console 9 includes the priority setting unit (in the embodiment, the input unit 7) that sets the priority for using the X-ray detector when the plurality of usable X-ray detectors (FPDs 3) exist among the X-ray detectors (in the embodiment, the FPDs 3) selected by the X-ray detector selecting unit (in the embodiment, the FPD selector 52). However, the priority is not necessarily set.

(13) In the embodiment, the console 9 includes the third X-ray detector choosing unit (in the embodiment, the third FPD choosing unit 55) when the inspection order information (imaging order information) is the recommended detector size. However, the console 9 does not necessarily include the third X-ray detector choosing unit (third FPD choosing unit 55) when the X-ray detector (in the embodiment, the FPD 3) having the uniform recommended detector size and the sensitivity and spatial resolution of rich variety. That is, when the recommended detector size is uniform, the flowcharts in FIG. 4 or 5 is not necessarily performed.

(14) In the embodiment, the highest-sensitivity X-ray detector (in the embodiment, the FPD 3) is chosen in the case that the sensitivity is considered. However, in the case that the sensitivity is not considered or in the case that the X-ray detector (FPD 3) with the uniform sensitivity is set, the highest-sensitivity X-ray detector (FPD 3) is not necessarily chosen.

REFERENCE SIGNS LIST

2 X-ray tube
3 flat panel X-ray detector (FPD)
5 controller
6A control program
7 input unit
51 FPD detector
52 FPD selector
53 first FPD choosing unit
54 second FPD choosing unit
55 third FPD choosing unit
56 first change setting unit

The invention claimed is:

1. An X-ray device comprising:
an X-ray tube that emits an X-ray;
an X-ray detector that detects the emitted X-ray;
an X-ray detector detecting unit that detects the X-ray detector that is usable;
an X-ray detector selecting unit that selects the X-ray detector to be chosen based on inspection order information,
wherein the X-ray detector selected by the X-ray detector selecting unit is chosen among X-ray detectors detected by the X-ray detector detecting unit,
wherein the inspection order information includes a recommended X-ray detector size to use for inspection, and
wherein the X-ray detector selecting unit selects the X-ray detector based on the recommended X-ray detector size, and
a first X-ray detector choosing unit that, when the X-ray detector having a size identical to the recommended X-ray detector size id usable, chooses the X-ray detector having the identical size, and when the X-ray detector having the size identical to the recommended X-ray detector size is unusable and the X-ray detector having a size larger than the recommended X-ray detector size is usable, chooses a smallest-size X-ray detector from the X-ray detectors having the larger size.

2. The X-ray device according to claim 1, further comprising a second X-ray detector choosing unit that chooses the corresponding X-ray detector when one X-ray detector having an identical size that is selected by the X-ray detector selecting unit exists among the X-ray detectors detected by the X-ray detector detecting unit.

3. The X-ray device according to claim 1, further comprising:
a priority setting unit that sets a priority for using the X-ray detector; and
a second X-ray detector choosing unit that chooses the X-ray detector according to the priority set by the priority setting unit,
wherein when a plurality of X-ray detectors having an identical size exist among the X-ray detectors detected by the X-ray detector detecting unit, the second X-ray detector choosing unit chooses the X-ray detector having top priority set by the priority setting unit from the plurality of X-ray detectors.

4. The X-ray device according to claim 1, wherein, when the X-ray detector having the size identical to the recommended X-ray detector size is unusable, the X-ray detector having the size larger than the recommended X-ray detector size is unusable, and the X-ray detector having a size smaller than the recommended X-ray detector size is usable, the first X-ray detector choosing unit chooses a largest-size X-ray detector from the X-ray detectors having the smaller size.

5. The X-ray device according to claim 1, wherein
the inspection order information is sensitivity of the X-ray detector in addition to the recommended X-ray detector size, and
the X-ray detector selecting unit selects the X-ray detector based on the recommended X-ray detector size among the X-ray detectors detected by the X-ray detector detecting unit, and chooses the X-ray detector having highest sensitivity from the corresponding X-ray detectors based on the usable X-ray detector.

6. The X-ray device according to claim 5, further comprising a second X-ray detector choosing unit that chooses the corresponding X-ray detector when one usable X-ray detector having the highest sensitivity exists.

7. The X-ray device according to claim 5, further comprising:
a priority setting unit that sets priority for using the X-ray detector; and
a third X-ray detector choosing unit that chooses the X-ray detector according to the priority set by the priority setting unit, wherein
when a plurality of usable X-ray detectors having the highest sensitivity exist, the third X-ray detector choosing unit chooses the X-ray detector having top priority that is set by the priority setting unit from the plurality of corresponding X-ray detectors.

8. The X-ray device according to claim 5,
wherein the X-ray detector having highest sensitivity is chosen from the corresponding X-ray detectors based on the usable X-ray detector among the smallest-size X-ray detectors chosen by a third X-ray detector choosing unit.

9. The X-ray device according to claim 8, wherein, when the X-ray detector having the size identical to the recommended X-ray detector size is unusable, the X-ray detector having the size larger than the recommended X-ray detector size is unusable, and the X-ray detector having a size smaller than the recommended X-ray detector size is usable, the third X-ray detector choosing unit chooses a largest-size X-ray detector from the X-ray detectors having the smaller size, and chooses the X-ray detector having the highest sensitivity from the corresponding X-ray detectors based on the usable X-ray detector among the largest-size X-ray detectors chosen by the third X-ray detector choosing unit.

10. The X-ray device according to claim 1, further comprising a change setting unit that changes setting of the unusable X-ray detector to the usable state, wherein the X-ray detector changed to the usable state by the change setting unit is chosen with top priority.

11. The X-ray device according to claim 1, further comprising a change setting unit that changes setting of the X-ray detector chosen as the usable X-ray detector to the unusable state, wherein when the X-ray detector is set to the unusable state by the change setting unit, selection is performed again by the X-ray detector selecting unit among the usable X-ray detectors detected by the X-ray detector detecting unit to choose the X-ray detector again.

12. The X-ray device according to claim 1, wherein one X-ray detector among the usable X-ray detectors is chosen with top priority.

13. A control device that controls the X-ray device according to claim 1, the control device comprising:

an X-ray detector detecting unit that detects a usable X-ray detector; and an X-ray detector selecting unit that selects an X-ray detector that is a choice target based on inspection order information, wherein the X-ray detector selected by the X-ray detector selecting unit is chosen among the X-ray detectors detected by the X-ray detector detecting unit.

14. A control method for controlling the X-ray device according to claim 1, the control method comprising:

an X-ray detector detecting step of detecting a usable X-ray detector; and an X-ray detector selecting step of selecting an X-ray detector that is a choice target based on inspection order information, wherein the X-ray detector selected in the X-ray detector selecting step is chosen among the X-ray detectors detected in the X-ray detector detecting step.

15. A non-transitory, tangible computer readable storage medium storing a control program, the control program configuring a computer to execute processing steps for controlling the X-ray device according to claim 1, the processing steps comprising:

an X-ray detector detecting step of detecting a usable X-ray detector; and an X-ray detector selecting step of selecting an X-ray detector that is a choice target based on inspection order information, wherein the X-ray detector selected in the X-ray detector selecting step is chosen among the X-ray detectors detected in the X-ray detector detecting step.

* * * * *